(12) United States Patent
Palmatier et al.

(10) Patent No.: US 10,195,050 B2
(45) Date of Patent: *Feb. 5, 2019

(54) EXPANDABLE INTERBODY IMPLANT AND METHODS OF USE

(71) Applicant: Warsaw Orthopedic, Inc., Warsaw, IN (US)

(72) Inventors: Stanley T. Palmatier, Olive Branch, MS (US); Keith E. Miller, Germantown, TN (US); Anthony J. Melkent, Memphis, TN (US); William D. Armstrong, Memphis, TN (US)

(73) Assignee: Warsaw Othopedic, Inc., Warsaw, IN (US)

(*) Notice: Subject to any disclaimer, the term of this patent is extended or adjusted under 35 U.S.C. 154(b) by 0 days.

This patent is subject to a terminal disclaimer.

(21) Appl. No.: 15/263,604

(22) Filed: Sep. 13, 2016

(65) Prior Publication Data
US 2016/0374826 A1    Dec. 29, 2016

Related U.S. Application Data

(62) Division of application No. 13/329,845, filed on Dec. 19, 2011, now Pat. No. 9,445,919.

(51) Int. Cl.
*A61F 2/44* (2006.01)
*A61F 2/30* (2006.01)
*A61F 2/28* (2006.01)

(52) U.S. Cl.
CPC ............ *A61F 2/447* (2013.01); *A61F 2/4425* (2013.01); *A61F 2/30965* (2013.01); *A61F 2002/2817* (2013.01); *A61F 2002/2835* (2013.01); *A61F 2002/304* (2013.01); *A61F 2002/3008* (2013.01); *A61F 2002/3037* (2013.01);
(Continued)

(58) Field of Classification Search
CPC .. A61F 2002/30471; A61F 2002/30624; A61F 2/4425; A61F 2/4455–2/447; A61F 2002/30515
See application file for complete search history.

(56) References Cited

U.S. PATENT DOCUMENTS 5,658,336 A    8/1997  Pisharodi
5,665,122 A    9/1997  Kambin
(Continued)

FOREIGN PATENT DOCUMENTS

KR    20050064501 A    6/2005

*Primary Examiner* — Jacqueline Johanas

(57) ABSTRACT

An intervertebral implant is provided. The intervertebral implant comprises a first component comprising an outer tissue engaging surface and an inner surface. A second component is connected to the first component, and is relatively moveable therefrom. The second component comprises an outer tissue engaging surface and an inner surface. The second component includes an actuator. A third component is disposed for engagement and is movable relative to the first and second components. The third component comprises at least a first ramp and a second ramp axially spaced apart from the first ramp. The actuator is engageable with the third component to effect axial translation of the wedge such that the ramps engage the inner surface of at least one of the first component and the second component to move the components between a first, collapsed configuration and a second, expanded configuration. Methods of use are disclosed.

20 Claims, 13 Drawing Sheets

(52) U.S. Cl.
CPC ........... *A61F 2002/30062* (2013.01); *A61F 2002/30092* (2013.01); *A61F 2002/3092* (2013.01); *A61F 2002/3093* (2013.01); *A61F 2002/30166* (2013.01); *A61F 2002/30266* (2013.01); *A61F 2002/30331* (2013.01); *A61F 2002/30357* (2013.01); *A61F 2002/30365* (2013.01); *A61F 2002/30369* (2013.01); *A61F 2002/30401* (2013.01); *A61F 2002/30405* (2013.01); *A61F 2002/30411* (2013.01); *A61F 2002/30433* (2013.01); *A61F 2002/30448* (2013.01); *A61F 2002/30469* (2013.01); *A61F 2002/30471* (2013.01); *A61F 2002/30492* (2013.01); *A61F 2002/30509* (2013.01); *A61F 2002/30515* (2013.01); *A61F 2002/30538* (2013.01); *A61F 2002/30556* (2013.01); *A61F 2002/30579* (2013.01); *A61F 2002/30601* (2013.01); *A61F 2002/30622* (2013.01); *A61F 2002/30624* (2013.01); *A61F 2002/30677* (2013.01); *A61F 2002/30774* (2013.01); *A61F 2002/30777* (2013.01); *A61F 2002/30785* (2013.01); *A61F 2002/30848* (2013.01); *A61F 2002/30878* (2013.01); *A61F 2002/30892* (2013.01); *A61F 2002/30904* (2013.01); *A61F 2002/443* (2013.01); *A61F 2002/4475* (2013.01); *A61F 2210/0004* (2013.01); *A61F 2220/0016* (2013.01); *A61F 2310/00017* (2013.01); *A61F 2310/00023* (2013.01); *A61F 2310/00029* (2013.01); *A61F 2310/00179* (2013.01); *A61F 2310/00221* (2013.01); *A61F 2310/00293* (2013.01); *A61F 2310/00341* (2013.01); *A61F 2310/00359* (2013.01); *A61F 2310/00976* (2013.01)

(56) References Cited

U.S. PATENT DOCUMENTS

| | | | |
|---|---|---|---|
| 5,782,832 A * | 7/1998 | Larsen | A61F 2/30742 623/17.11 |
| 5,980,522 A | 11/1999 | Koros et al. | |
| 6,102,950 A | 8/2000 | Vaccaro | |
| 6,299,642 B1 | 10/2001 | Chan | |
| 6,419,705 B1 * | 7/2002 | Erickson | A61F 2/4455 623/17.11 |
| 6,491,724 B1 | 12/2002 | Ferree | |
| 6,835,206 B2 | 12/2004 | Jackson | |
| 6,955,691 B2 | 10/2005 | Chae et al. | |
| 7,070,598 B2 | 7/2006 | Lim | |
| 7,087,055 B2 | 8/2006 | Lim | |
| 7,118,579 B2 | 10/2006 | Michelson | |
| 7,214,243 B2 | 5/2007 | Taylor | |
| 7,320,555 B2 | 1/2008 | Chang et al. | |
| 7,410,501 B2 | 8/2008 | Michelson | |
| 7,445,636 B2 | 11/2008 | Michelson | |
| 7,621,960 B2 | 11/2009 | Boyd et al. | |
| 7,655,027 B2 | 2/2010 | Michelson | |
| 7,655,046 B2 | 2/2010 | Dryer | |
| 7,753,958 B2 | 7/2010 | Gordon | |
| 7,763,078 B2 | 7/2010 | Peterman et al. | |
| 7,828,849 B2 | 11/2010 | Lim | |
| 7,846,185 B2 | 12/2010 | Carls et al. | |
| 7,850,733 B2 | 12/2010 | Baynham et al. | |
| 7,875,078 B2 | 1/2011 | Wysocki et al. | |
| 7,909,869 B2 | 3/2011 | Gordon et al. | |
| 8,062,375 B2 | 11/2011 | Glerum et al. | |
| 8,105,358 B2 | 1/2012 | Phan | |
| 8,105,382 B2 | 1/2012 | Olmos et al. | |
| 8,123,810 B2 | 2/2012 | Gordon et al. | |
| 8,133,232 B2 | 3/2012 | Levy et al. | |
| 8,187,332 B2 | 5/2012 | Mcluen | |
| 8,382,842 B2 | 2/2013 | Greenhalgh et al. | |
| 8,394,145 B2 | 3/2013 | Weiman | |
| 8,398,713 B2 | 3/2013 | Weiman | |
| 8,403,990 B2 | 3/2013 | Dryer et al. | |
| 8,435,298 B2 | 5/2013 | Weiman | |
| 8,491,659 B2 | 7/2013 | Weiman | |
| 8,518,120 B2 | 8/2013 | Glerum et al. | |
| 8,523,944 B2 | 9/2013 | Jimenez et al. | |
| 8,556,979 B2 | 10/2013 | Weiman et al. | |
| 8,568,481 B2 | 10/2013 | Olmos | |
| 8,628,577 B1 | 1/2014 | Jimenez | |
| 8,628,578 B2 | 1/2014 | Miller et al. | |
| 8,632,595 B2 | 1/2014 | Weiman | |
| 8,663,329 B2 | 3/2014 | Ernst | |
| 8,679,183 B2 | 3/2014 | Glerum et al. | |
| 8,685,098 B2 | 4/2014 | Glerum et al. | |
| 8,709,086 B2 | 4/2014 | Glerum et al. | |
| 8,778,025 B2 | 7/2014 | Ragab et al. | |
| 8,795,366 B2 | 8/2014 | Varela | |
| 8,888,853 B2 | 11/2014 | Glerum et al. | |
| 8,888,854 B2 | 11/2014 | Glerum et al. | |
| 8,894,711 B2 | 11/2014 | Varela | |
| 8,894,712 B2 | 11/2014 | Varela | |
| 8,926,704 B2 | 1/2015 | Glerum | |
| 8,940,049 B1 | 1/2015 | Jimenez | |
| 9,039,771 B2 | 5/2015 | Glerum et al. | |
| 9,119,730 B2 | 9/2015 | Glerum et al. | |
| 9,788,971 B1 * | 10/2017 | Stein | A61F 2/447 |
| 9,801,734 B1 * | 10/2017 | Stein | A61F 2/447 |
| 2002/0068976 A1 | 6/2002 | Jackson | |
| 2002/0068977 A1 | 6/2002 | Jackson | |
| 2004/0010315 A1 | 1/2004 | Song | |
| 2004/0087947 A1 | 5/2004 | Lim | |
| 2004/0249466 A1 | 12/2004 | Liu et al. | |
| 2005/0113916 A1 | 5/2005 | Branch, Jr. | |
| 2005/0113917 A1 | 5/2005 | Chae et al. | |
| 2006/0241643 A1 | 10/2006 | Lim | |
| 2006/0241770 A1 | 10/2006 | Rhoda | |
| 2006/0247778 A1 | 11/2006 | Ferree et al. | |
| 2008/0058938 A1 | 3/2008 | Mujwid | |
| 2009/0112319 A1 | 4/2009 | O'Neil | |
| 2009/0171461 A1 | 7/2009 | Conner | |
| 2009/0228109 A1 | 9/2009 | Pointillant et al. | |
| 2010/0057208 A1 | 3/2010 | Dryer | |
| 2010/0204795 A1 | 8/2010 | Greenhalgh | |
| 2010/0217397 A1 | 8/2010 | Pointillart et al. | |
| 2010/0286780 A1 | 11/2010 | Dryer | |
| 2010/0286783 A1 | 11/2010 | Lechmann | |
| 2010/0292796 A1 | 11/2010 | Greenhalgh | |
| 2011/0029082 A1 | 2/2011 | Hall | |
| 2011/0054621 A1 | 3/2011 | Lim | |
| 2011/0172721 A1 | 7/2011 | Varela | |
| 2011/0172774 A1 | 7/2011 | Varela | |
| 2011/0301711 A1 | 12/2011 | Palmatier et al. | |
| 2012/0035729 A1 | 2/2012 | Glerum et al. | |
| 2012/0109319 A1 | 5/2012 | Perisic | |
| 2012/0150304 A1 | 6/2012 | Glerum et al. | |
| 2012/0150305 A1 | 6/2012 | Glerum et al. | |
| 2012/0158146 A1 | 6/2012 | Glerum et al. | |
| 2012/0158147 A1 | 6/2012 | Glerum et al. | |
| 2012/0158148 A1 | 6/2012 | Glerum et al. | |
| 2013/0144388 A1 | 6/2013 | Emery et al. | |
| 2013/0158664 A1 | 6/2013 | Palmatier et al. | |
| 2014/0121774 A1 | 5/2014 | Glerum et al. | |
| 2014/0324171 A1 | 10/2014 | Glerum et al. | |

\* cited by examiner

EXPANDABLE INTERBODY IMPLANT AND METHODS OF USE

CROSS REFERENCE TO RELATED APPLICATIONS

This application is a divisional application of U.S. patent application Ser. No. 13/329,845, filed Dec. 19, 2011, which is incorporated by reference herein, in its entirety.

TECHNICAL FIELD

The present disclosure generally relates to medical devices, systems and methods for the treatment of musculoskeletal disorders, and more particularly to an expandable interbody implant system and method for treating a vertebral column.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy and implantable prosthetics. These treatments may employ interbody implants. This disclosure describes an improvement over these prior art technologies.

SUMMARY

Accordingly, an expandable interbody implant system and method are disclosed. In one embodiment, an intervertebral implant is provided. The intervertebral implant comprises a first component comprising an outer tissue engaging surface and an inner surface. A second component is connected to the first component, and is relatively moveable therefrom. The second component comprises an outer tissue engaging surface and an inner surface. The second component includes an actuator. A third component is disposed for engagement and is movable relative to the first and second components. The third component comprises at least a first ramp and a second ramp axially spaced apart from the first ramp. The actuator is engageable with the third component to effect axial translation of the wedge such that the ramps engage the inner surface of at least one of the first component and the second component to move the components between a first, collapsed configuration and a second, expanded configuration.

In one embodiment, an intervertebral implant comprises a piston component comprising an endplate surface and an inner surface disposed in an opposing orientation relative to the endplate surface. The piston component extends between an anterior end and a posterior end. A base component comprises an endplate surface and an inner surface disposed in an opposing orientation relative to the endplate surface of the base component. The base component extends between an anterior end and a posterior end. The base component is pivotably connected to the piston component adjacent the respective posterior ends. The posterior end of the base component includes a threaded cavity. A threaded screw is configured for disposal within the threaded cavity. A wedge is disposed for engagement and is movable relative to the piston and base components. The wedge comprises a first ramp having a first height and a first angle of inclination and a second ramp having a second height and a second angle of inclination. The first ramp is axially spaced apart from the second ramp. The threaded screw is engageable with the wedge to effect axial translation of the wedge such that the ramps engage the inner surface of the first component to pivot the first component relative to the second component such that the components expand between a first, collapsed configuration and a second, expanded configuration.

In one embodiment, a method for treating a spine is provided. The method comprises the steps of: providing an intervertebral implant comprising: a first component having an anterior end and a posterior end, the first component comprising an outer tissue engaging surface and an inner surface; a second component having an anterior end and a posterior end, the second component being pivotably connected to the first component adjacent the respective posterior ends, the second component comprising an outer tissue engaging surface and an inner surface, the second component including an actuator, and a third component disposed for engagement and being movable relative to the first and second components, the third component comprising at least a first ramp and a second ramp axially spaced apart from the first ramp; introducing the intervertebral implant in a collapsed configuration along a substantially posterior approach of a body within an intervertebral space; and engaging the actuator with the third component to effect axial translation of the third component relative to the first and second components such that the ramps engage the inner surface of at least one of the first component and the second component to expand the intervertebral implant to a second, expanded configuration.

BRIEF DESCRIPTION OF THE DRAWINGS

The present disclosure will become more readily apparent from the specific description accompanied by the following drawings, in which.

DETAILED DESCRIPTION

Figure 1:
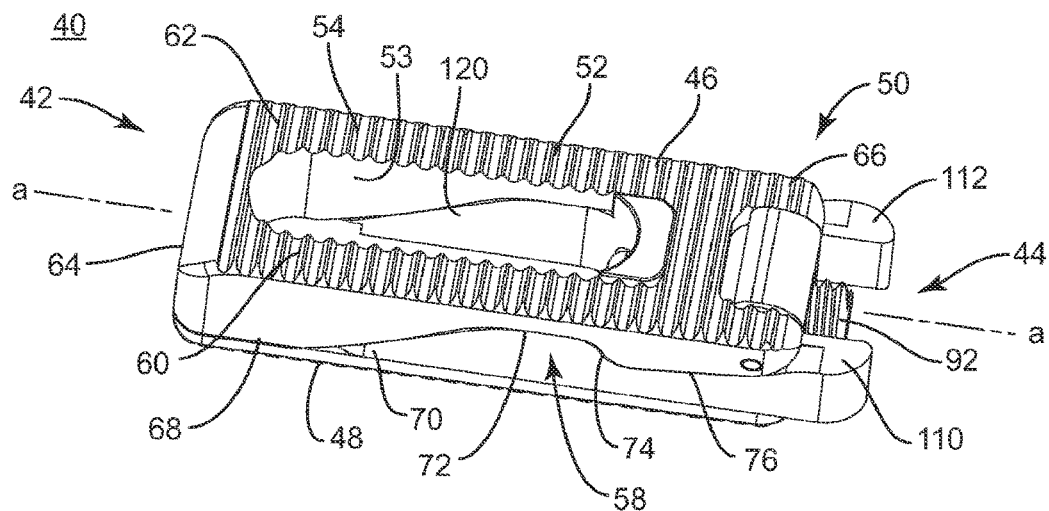
FIG. 1 is a perspective view of one particular embodiment of an implant of a system in accordance with the principles of the present disclosure.
Figure 2:
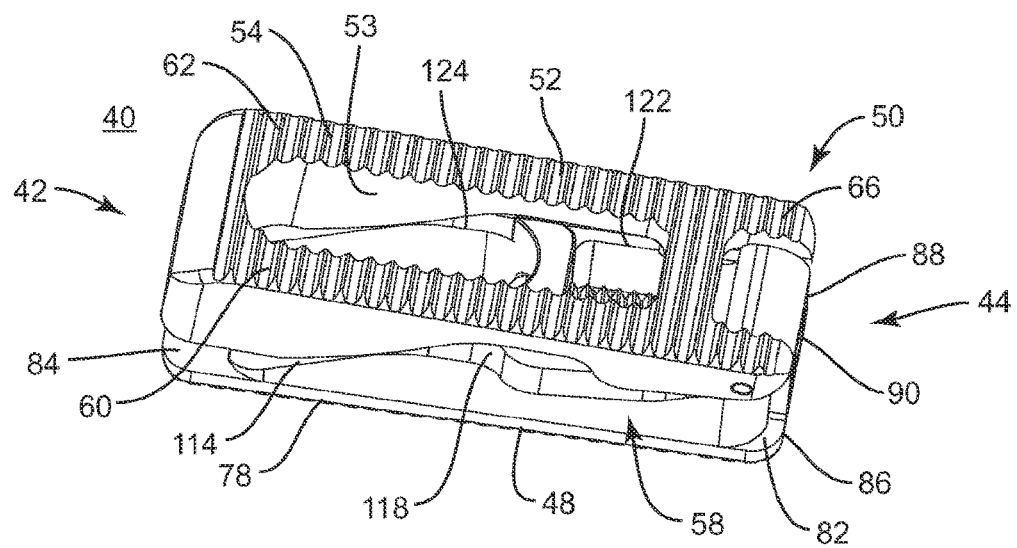
FIG. 2 is a perspective view of the implant shown in FIG. 1.
Figure 3:
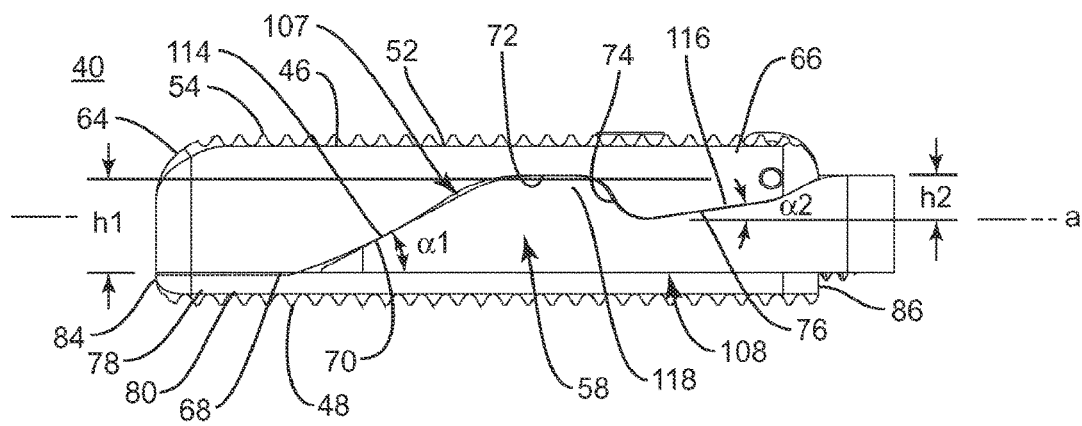
FIG. 3 is a side view of the implant shown in FIG. 1.
Figure 4:
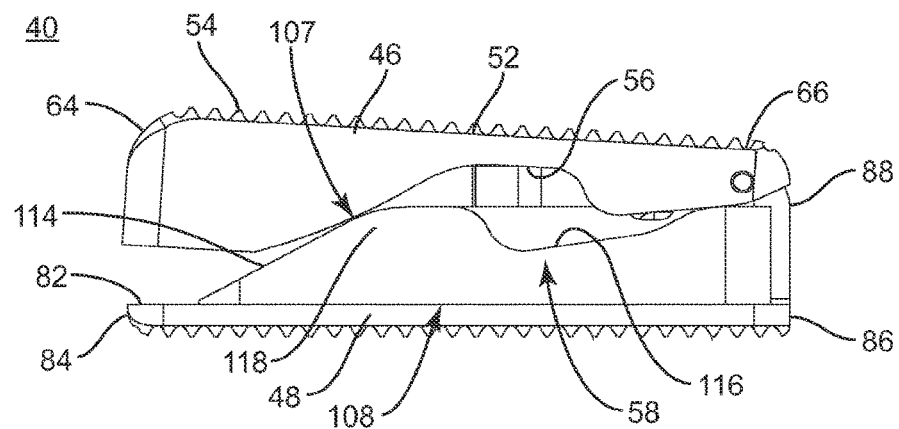
FIG. 4 is a side view of the implant shown in FIG. 1.

The exemplary embodiments of an expandable interbody implant system and related methods of use disclosed herein are discussed in terms of medical devices for the treatment of musculoskeletal disorders and more particularly, in terms of an expandable interbody implant system and related methods for treating a vertebral column. It is envisioned that the implant system may provide, for example, fusion, decompression, restoration of sagittal balance and resistance of subsidence into tissue, such as, for example, surfaces of vertebral endplates. It is further envisioned that the system includes an interbody implant that expands after insertion into an intervertebral disc space and has several features, such as, for example, facile insertion into the intervertebral disc space such that less bone removal is necessary during a surgical procedure, decompression of nerve roots, expansion to restore sagittal balance such that more expansion is provided on an anterior side relative to a posterior side in for example a lumbar application.

In one embodiment, the expandable interbody implant system is employed with a posterior approach to the intervertebral disc space such that a distal end of the interbody implant expands more than a proximal end of the interbody implant to restore lordosis. In one embodiment, the expandable interbody implant includes a base component that engages a first vertebral endplate, a piston component that engages a second vertebral endplate disposed in an opposing orientation and a double ramp component that is driven between the base and piston components to drive the base and piston components apart. It is contemplated that the double ramp component is moved relative to the base component via a male threaded component. It is further contemplated that the double ramp includes two wedges that drive apart the piston and base components at the proximal and distal ends of the expandable interbody implant. It is envisioned that the height and angle of each wedge selectively provides an amount and rate of expansion on each end of the expandable interbody implant. For example, a steeper and/or taller wedge on a distal and/or anterior portion of the expandable interbody implant drives lordosis as the interbody implant is expanded.

It is envisioned that the expandable interbody implant and methods of use disclosed herein can be employed to obtain fusion of vertebrae through a minimally invasive or percutaneous technique. In one embodiment, the disclosed expandable interbody implant and methods of use can provide improved spinal treatment with a device that is made to expand vertically to create lordosis in vertebrae. It is contemplated that the expandable interbody implant and methods of use disclosed herein provide a cavity of relatively large volume for post-packing of at least one agent, for example, bone graft.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed expandable interbody implant may be alternatively employed in a surgical treatment with a patient in a prone or supine position, and/or employ various surgical approaches to the spine, including anterior, posterior, posterior mid-line, medial, lateral, postero-lateral, and/or antero-lateral approaches, and in other body regions. The expandable interbody implant of the present disclosure may also be alternatively employed with procedures for treating the lumbar, cervical, thoracic and pelvic regions of a spinal column. The expandable interbody implant and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

Further, as used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of an expandable interbody implant and related methods of employing the expandable interbody implant in accordance with the principles of the present disclosure. Alternate embodiments are also disclosed. Reference will now be made in detail to the exemplary embodiments of the present disclosure, which are illustrated in the accompanying figures. Turning now to FIGS. 1-4, there is illustrated components of an interbody implant system including an intervertebral implant 40 in accordance with the principles of the present disclosure.

The components of the system can be fabricated from biologically acceptable materials suitable for medical applications, including metals, synthetic polymers, ceramics and bone material and/or their composites, depending on the particular application and/or preference of a medical practitioner. For example, the components of the system, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (for example, Nitinol, super elasto-plastic metals, such as GUM METAL® manufactured by Toyota Material Incorporated of Japan), ceramics and composites thereof such as calcium phosphate (for example, SKELITE™ manufactured by Biologix Inc.), thermoplastics such as polyaryl ether ketone (PAEK) including polyether ether ketone (PEEK), polyether ketone ketone (PEKK) and polyetherketone (PEK), carbon-PEEK composites, PEEK-$BaSO_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polylactide, polyglycolide, polytyrosine carbonate, polycaprolactone and their combinations. Various components of the system may be fabricated from material composites, including the above materials, to achieve various desired characteristics such as strength, rigidity, elasticity, flexibility, compliance, biomechanical performance, durability and radiolucency or imaging preference. The components of the system, individually or collectively, may also be fabricated from a heterogeneous material such as a combination of two or more of the above-described materials.

The system including intervertebral implant 40 can be employed as a stabilization device in fusion and fixation procedures, for example, for patients suffering from a spinal disorder to provide height restoration between vertebral bodies, decompression, restoration of sagittal balance and/or resistance of subsidence into vertebral endplates. The components of the interbody implant system may be monolithically formed, integrally connected or include fastening elements and/or instruments, for example, as described herein.

Intervertebral implant 40 defines a longitudinal axis a and extends between a first end, such as, for example, an anterior end 42 and a second end, such as, for example, a posterior end 44. Intervertebral implant 40 includes a first component, such as, for example, a piston component 46 and a second component, such as, for example, a base component 48 connected to piston component 46. Base component 48 is movably mounted to piston component 46 with a hinge 50 to facilitate a pivoting connection between components 46, 48. Components 46, 48 are relatively movable to expand and collapse with intervertebral implant 40 between a first configuration and a second configuration, as will be described. It is contemplated that components 46, 48 may be monolithically formed and/or be connected via a living hinge. It is further contemplated that base component 48 may be alternatively connected to piston component 42 by integral connection, press fit, threaded, adhesive and/or fastening elements such as clips and/or screws. It is envisioned that intervertebral implant 40 may include one or a plurality of components.

Piston component 46 includes an outer tissue engaging surface, such as, for example, an endplate surface 52. Endplate surface 52 defines a substantially rectangular opening 53 extending therethrough. It is envisioned that opening 53 may be configured for packing of at least one agent, for example, bone graft. It is further envisioned that opening 53 may have alternate configurations, such as, for example, oval, oblong, triangular, square, polygonal, irregular, uniform, non-uniform, offset, staggered, undulating, arcuate, variable and/or tapered. It is contemplated that endplate surface 52 may include one or a plurality of openings.

Endplate surface 52 is configured to engage an endplate of a vertebra and includes a plurality of raised elements 54 configured to enhance fixation and/or gripping with vertebral tissue. Elements 54 are disposed transverse to longitudinal axis a. It is envisioned that all or only a portion of endplate surface 52 may have alternate surface configurations to enhance fixation with tissue such as, for example, rough, arcuate, undulating, mesh, porous, semi-porous, dimpled and/or textured according to the requirements of a particular application. It is further envisioned that elements 54 may be disposed at alternate orientations, relative to axis a, such as, for example, perpendicular and/or other angular orientations such as acute or obtuse, co-axial and/or may be offset or staggered.

Piston component 46 includes an inner surface 56 disposed to face an opposing orientation and/or direction relative to the facing orientation and/or direction of endplate surface 52. Endplate surface 52 is oriented in a direction to face tissue of a vertebral endplate and inner surface 56 is oriented to face an opposite direction. Inner surface 56 is substantially smooth or even and configured to engage a surface of a third component, such as, for example, a wedge 58 such that wedge 58 is movable relative to components 46, 48.

Piston component 46 includes a first extension 60 and a second extension 62 extending in a substantially linear configuration along longitudinal axis a between a first end, such as, for example, an anterior end 64 and a second end, such as, for example, a posterior end 66. Extensions 60, 62 are monolithically formed with ends 64, 66. It is envisioned that extensions 60, 62 may be alternatively connected to ends 64, 66 by integral connection, press fit, threaded, adhesive and/or fastening elements such as hinge, clip and/or screws. Extensions 60, 62 are disposed in a substantially parallel orientation relative to longitudinal axis a. It is contemplated that extensions 60 and/or 62 may be disposed at alternate orientations, relative to longitudinal axis a, for example, perpendicular, converging, diverging and/or other angular orientations such as acute or obtuse, co-axial and/or may be offset or staggered. It is envisioned that extensions 60, 62 may extend in alternate configurations such as, for example, radius of curvature, offset and/or staggered. It is further envisioned that extensions 60, 62 may have various cross section configurations, such as, for example, oval, oblong, triangular, rectangular, square, polygonal, irregular, uniform, non-uniform, variable, hollow and/or tapered.

Each of extensions 60, 62 include at least a portion of inner surface 56 that engages at least a portion of the surface of wedge 58 to expand and collapse intervertebral implant 40 between a first configuration and a second configuration, as will be described. For example, each of extensions 60, 62 include a planar portion 68 that engages base component 48, a first inclined portion 70, a recess portion 72, a transition 74 and a second inclined portion 76. Portions 68, 70, 72, 74, 76 are disposed in series along each of extensions 60, 62. Inclined portions 70, 76 are disposed at an angle from axis a.

Base component 48 includes an outer tissue engaging surface, such as, for example, an endplate surface 78. It is envisioned that endplate surface 78 may include one or a plurality of openings configured for packing of at least one agent, for example, bone graft. Endplate surface 78 is configured to engage an endplate of a vertebra and includes a plurality of raised elements 80 configured to enhance fixation and/or gripping with vertebral tissue. Elements 80 are disposed transverse to longitudinal axis a. It is envisioned that all or only a portion of surface 78 may have alternate surface configurations to enhance fixation with tissue similar to those alternatives described herein. It is further envisioned that elements 80 may be disposed at alternate orientations, relative to longitudinal axis a, similar to those alternatives described herein.

Base component 48 includes an inner surface 82 disposed to face an opposing orientation and/or direction relative to the facing orientation and/or direction of endplate surface 78. Endplate surface 78 is oriented in a direction to face tissue of a vertebral endplate and inner surface 82 is oriented to face an opposite direction. Inner surface 82 is planar and substantially smooth or even and configured to engage a surface of wedge 58. Inner surface 82 engages the surface of wedge 58 such that wedge 58 is movable relative to components 46, 48.

Base component 48 extends in a substantially linear configuration along longitudinal axis a between a first end, such as, for example, an anterior end 84 and a second end, such as, for example, a posterior end 86. Posterior end 86 includes a wall 88 that defines an elongated cavity, such as, for example, threaded opening 90. An actuator, such as, for example, a threaded screw 92 is configured for disposal within threaded opening 90 and extends to a distal end 94 that is fixed with wedge 58.

Screw 92 is rotatable relative to wall 88 in a first direction, such as clockwise, and a second opposing direction, such as counter clockwise. Screw 92 is configured to mate with threaded opening 90 in a threaded engagement and distal end 94 is fixed with wall 98 and freely rotatable therein. Screw 92 is caused to engage opening 90 and rotated in a selected direction such that screw 92 is threaded with opening 90. Screw 92 is configured for translation relative to wall 88 in a first axial direction and a second axial direction.

Figure 5:
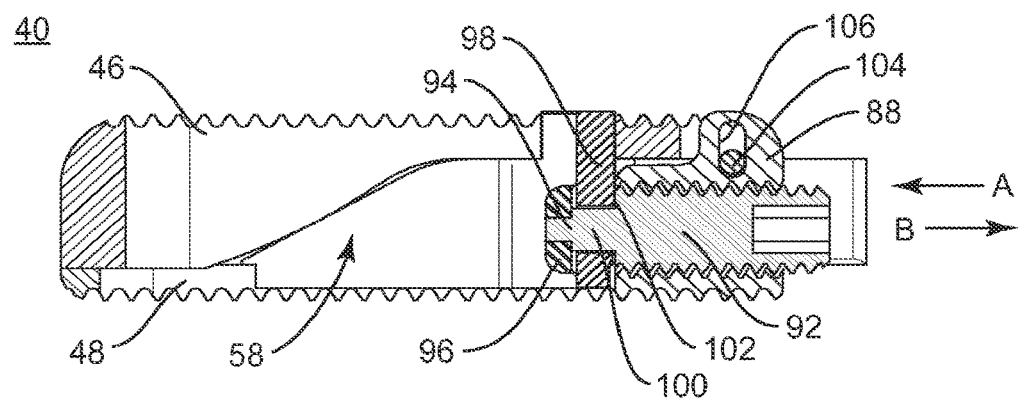
FIG. 5 is a side cross section view of the implant shown in FIG. 1.
Figure 6:
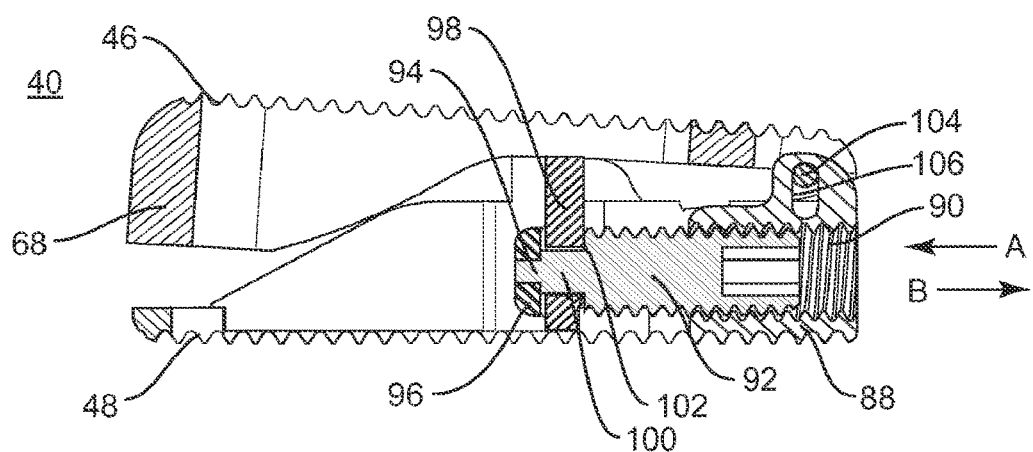
FIG. 6 is a side cross section view of the implant shown in FIG. 1.

Distal end 94 includes a flange 96 that engages a wall 98 of wedge 58 to retain screw 92 with wedge 58, as shown in FIGS. 5 and 6. Distal end 94 extends through wall 98 and includes a reduced diameter 100 such that distal end 94 rotates relative to wall 98 to facilitate axial translation of screw 92 and wedge 58. Reduced diameter 100 facilitates engagement of an adjacent surface 102 of screw 92 with wall 98 to drive and axially translate wedge 58, in a first direction shown by arrow A. Flange 96 engages wall 98 to draw and axially translate wedge 58, in a second opposing direction shown by arrow B.

Screw 92 is fixed with wedge 58 to effect axial translation of wedge 58 such that wedge 58 is movable relative to components 46, 48 to expand and collapse intervertebral implant 40 between a first configuration and a second configuration, as will be described. Screw 92 is engaged with an instrument or tool (not shown), to facilitate actuation of the component parts of intervertebral implant 40 and disposal thereof in various configurations according to the requirements of a particular application.

Base component 48 is pivotably connected to piston component 46 adjacent posterior ends 66, 86 with hinge 50 to facilitate a pivoting connection between components 46, 48. Posterior end 66 includes a pin 104 configured for disposal within an elongated slot 106 of posterior end 86. Pin 104 is movable along an axis transverse to longitudinal axis a along slot 106 to facilitate expansion and collapse of intervertebral implant 40 between a first configuration and a second configuration.

Wedge 58 is disposed in an intermediate orientation with components 46, 48. Wedge 58 includes a first surface 107 that engages component 46 and a second surface 108 that engages component 48 such that wedge 58 is movable for axial translation relative to components 46, 48. Wedge 58 includes a first rail portion 110 and a second rail portion 112, disposed along longitudinal axis a, which movably engage components 46, 48 to expand and collapse intervertebral implant 40 between a first configuration and a second configuration.

Rail portion 110 includes a first ramp, such as, for example, an anterior wedge portion 114 and a second ramp, such as, for example, a posterior wedge portion 116. Anterior wedge portion 114 is axially spaced apart from posterior wedge portion 116 along rail portion 110. Anterior wedge portion 114 has a first height h1 and a first angle of inclination α1 relative to longitudinal axis a. It is envisioned that height h1 may be in a range of 3-7 millimeters (mm). It is further envisioned that angle α1 may be in a range of 30 to 60 degrees.

Posterior wedge portion 116 has a second height h2 and a second angle of inclination α2 relative to axis a. It is envisioned that height h2 may be in a range of 1 to 5 mm. It is envisioned that angle α2 may be in a range of 4 to 30 degrees. In one embodiment, height h1 is greater than height h2. In one embodiment, angle α1 is greater than angle α2.

Rail portion 110 includes a protrusion 118 disposed between wedge portions 114, 116 such that wedge portions 114, 116 are axially spaced apart and also connecting wedge portion 114 with wedge portion 116. Wedge portions 114, 116 and protrusion 118 are disposed in series along rail portion 110. It is contemplated that wedge portions 114, 116 drive apart components 46, 48 at anterior end 42 and posterior end 44 to facilitate expansion and collapse of intervertebral implant 40 between a first configuration and a second configuration. It is further contemplated that the height and/or angle of wedge portions 114, 116 regulates the amount and rate of expansion of intervertebral implant 40 at least adjacent rail portion 110. It is envisioned that wedge portions 114, 116 are monolithically formed, connected by fastening elements or separate and distinct structure.

Rail portion 112 includes a third ramp, such as, for example, an anterior wedge portion 120 and a fourth ramp, such as, for example, a posterior wedge portion 122. Anterior wedge portion 120 is axially spaced apart from posterior wedge portion 122 along rail portion 112. Anterior wedge portion 120 has height h1 and angle of inclination α1. Posterior wedge portion 122 has height h2 and angle of inclination α2.

Rail portion 112 includes a protrusion 124 disposed between wedge portions 120, 122 such that wedge portions 120, 122 are axially spaced apart. Protrusion 124 connects wedge portion 120 with wedge portion 122. Wedge portions 120, 122 and protrusion 124 are disposed in series along rail portion 112. It is contemplated that wedge portions 120, 122 drive apart components 46, 48 at anterior end 42 and posterior end 44 to facilitate expansion and collapse of intervertebral implant 40 between a first configuration and a second configuration. It is further contemplated that the height and/or angle of wedge portions 120, 122 regulates the amount and rate of expansion of intervertebral implant 40 at least adjacent rail portion 112. It is envisioned that wedge portions 120, 122 are monolithically formed, connected by fastening elements or separate and distinct structure.

Each of rail portions 110, 112 include at least a portion of first surface 107 that engages at least a portion of inner surface 56 of component 46 to expand and collapse intervertebral implant 40 between a first configuration and a second configuration. For example, the portions of surface 107 including wedge portions 114, 116 and protrusion 118 disposed along rail portion 110 slideably engage portions 68, 70, 72, 74, 76 disposed along extension 60. The portions of surface 107 including wedge portions 120, 122 and protrusion 124 disposed along rail portion 112 slideably engage portions 68, 70, 72, 74, 76 disposed along extension 62. Each of rail portions 110, 112 also include at least a portion of surface 108 that slidably engages at least a portion of inner surface 82 corresponding to extensions 60, 62.

Rail portions 110, 112 extend in a proximal and/or posterior direction for disposal about wall 88 adjacent posterior end 44. Rail portions 110, 112 move about wall 88 during axial translation of the component parts of intervertebral implant 40.

Figure 7:
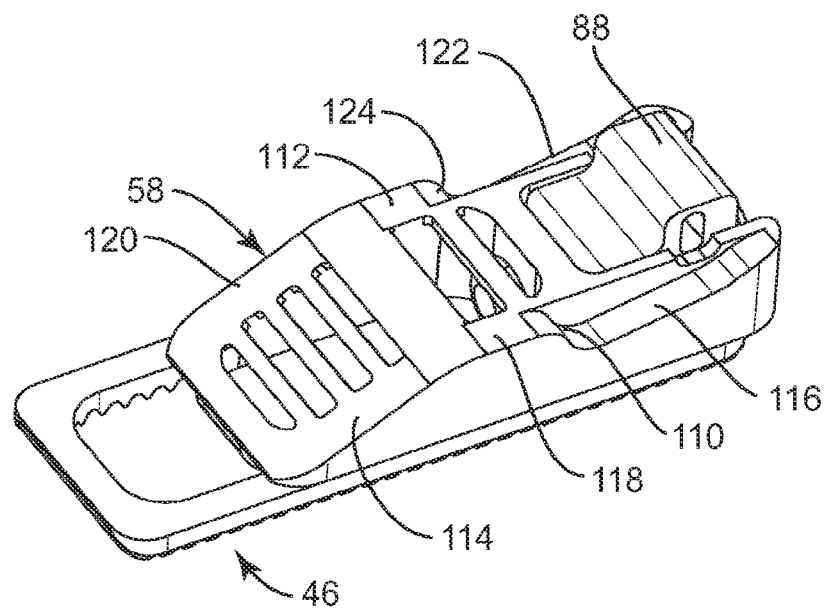
FIG. 7 is a perspective view of one embodiment of the components of the implant shown in FIG. 1.
Figure 8:
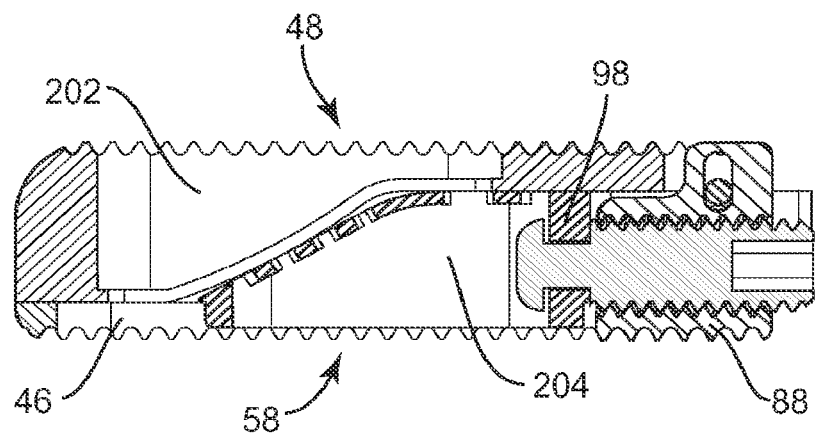
FIG. 8 is a perspective cutaway view of the implant shown in FIG. 1.

In one embodiment, as shown in FIGS. 7 and 8, piston component 48 includes a receptacle, such as, for example, a basket 202 configured for disposal of at least one agent, for example, bone graft. Wedge 58 includes a receptacle, such as, for example, a basket 204 configured for disposal of at least one agent, for example, bone graft. In the first, collapsed configuration, baskets 202, 204 are disposed in series in a side by side configuration. As intervertebral implant 40 is expanded to the second, expanded configuration, baskets 202, 204 translate to a vertical stacked configuration such that bone graft can grow through the connected baskets 202, 204. Each of baskets 202, 204 include a plurality of openings that allow bone to grow between baskets 202, 204. In one embodiment, basket 202 is an upper basket having a constant volume and basket 204 is a lower basket having a constant volume. Baskets 202, 204 are packed with bone graft prior to delivery to a surgical site and disposed in series in a side by side configuration. Baskets 202, 204 have ramped interfaces that allows baskets 202, 204 to maintain contact therebetween as intervertebral implant 40 expands from the first, collapsed configuration to the second, expanded configuration, and baskets 202, 204 transition from a side by side configuration to a stacked and/or top to bottom configuration. This interface between baskets 202, 204 has openings so that bone graft in one of baskets 202, 204 can interface with bone graft in the other of baskets 202, 204. This configuration allows bone graft to fuse from a first vertebral endplate through basket 202 and through basket 204, or vice versa, to a second vertebral endplate.

Figure 9:
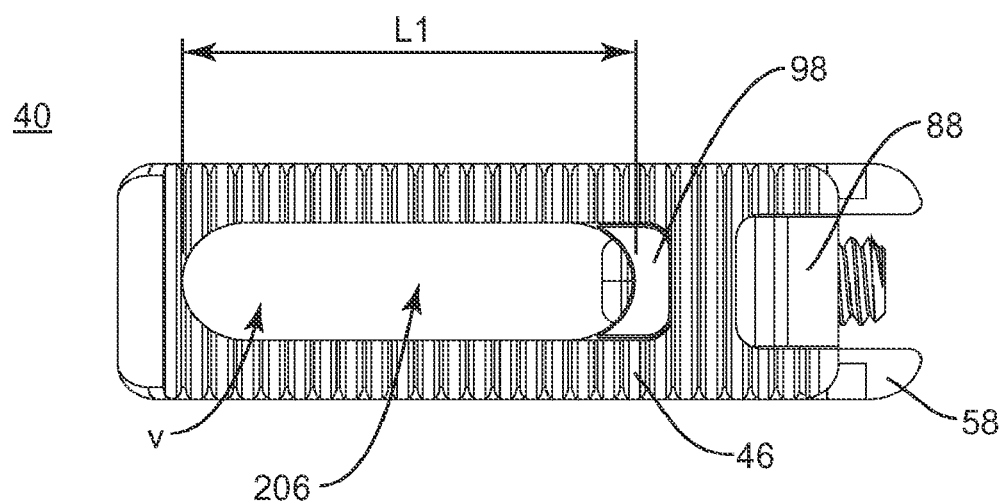
FIG. 9 is a plan view of one embodiment of the implant shown in FIG. 1.
Figure 10:
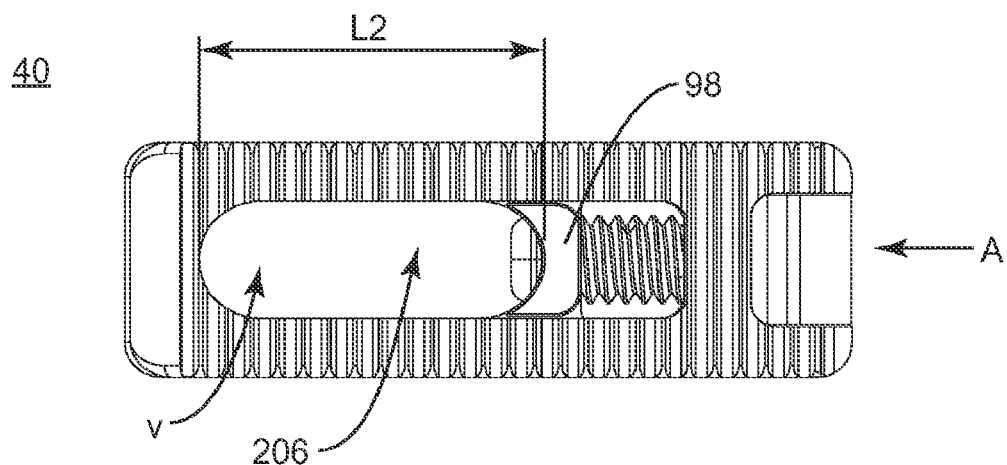
FIG. 10 is a plan view of the implant shown in FIG. 9.

In one embodiment, as shown in FIGS. 9 and 10, intervertebral implant 40 includes a bone graft cavity configured to have a controlled volume of bone graft disposed with intervertebral implant 40. Intervertebral implant 40 includes an opening 206 extending through its body and components 46, 48 and 58. Opening 206 is configured for disposal of at least one agent, for example, bone graft. In the first, collapsed configuration, opening 206 defines a length L1 and cross sectional area such that a volume v of bone graft is disposed within opening 206. Wall 98 of wedge 58 is disposed in a proximal or posterior position. As intervertebral implant 40 is expanded to the second, expanded configuration, the overall height of implant 40 increases and wall 98 is translated axially in the direction shown by arrow A in FIG. 6, as described herein. As wall 98 axially translates, the cross-sectional area of opening 206 is decreased. Wall 98 is translated to a distal or anterior position such that opening 206 defines a length L2. The components of intervertebral implant 40 are dimensioned such that a decrease in length of opening 206 to length L2 and the increase in height of intervertebral implant 40 are combined to maintain a substantially constant volume V of bone graft throughout expansion of intervertebral implant 40. This allows intervertebral implant 40 to maintain a constant volume of bone graft at any height of expansion. It is contemplated that this configuration for maintaining bone graft volume avoids the bone graft becoming loose within opening 206 as intervertebral implant 40 increases in height. It is further contemplated that tightly packed bone graft can potentially increase fusion capability. In one embodiment, intervertebral implant 40 provides a controlled volume of bone graft such that the components of intervertebral implant 40 are dimensioned such that a decrease in length of opening 206 to length L2 occurs at a faster rate than the increase in height of intervertebral implant 40. As such, the volume of bone graft is decreased as intervertebral implant 40 expands. This configuration of intervertebral implant 40 compresses the bone graft as intervertebral implant 40 is expanded. It is contemplated that the compressed bone graft within intervertebral implant 40 can increase the likelihood of fusion to occur from a first vertebral body through the bone graft into a second vertebral body.

In operation, as shown in FIGS. 3-6, intervertebral implant 40 is engaged for disposal between a first configuration and a second configuration such that intervertebral implant 40 expands in an intervertebral disc space. Intervertebral implant 40 is engaged with an instrument (not shown) to facilitate actuation of the component parts of intervertebral implant 40 according to the requirements of a particular surgical application.

In a first configuration, such as, for example, a collapsed configuration (FIG. 5), components 46, 48 are disposed in a low profile orientation with wedge 58 such that planar portions 68 of extensions 60, 62 are disposed in flush engagement with inner surface 82. Wedge portions 114, 120 are disposed in flush engagement with the respective inclined portions 70 of extensions 60, 62 and wedge portions 116, 122 are disposed in engagement with the respective inclined portions 76 of extensions 60, 62. Protrusions 118, 124 are disposed within the respective recess portions 72 of extensions 60, 62.

Upon desired positioning of intervertebral implant 40 according to the requirements of a particular surgical application, screw 92 is manipulated to move wedge 58 axially. The instrument engages screw 92 for rotation in a clockwise direction. Screw 92 translates axially in a first axial direction shown by arrow A. As screw 92 translates axially, surface 102 engages wall 98 to drive wedge 58 axially in the direction shown by arrow A. Wedge portions 114, 120 slidably engage the respective inclined portions 70 of extensions 60, 62 and wedge portions 116, 122 slidably engage the respective inclined portions 76 of extensions 60, 62. Such slidable engagement of the surfaces of wedge 58 and components 46, 48, due to the axial translation of wedge 58, pivots component 46 relative to component 48 in rotation about hinge 50 such that components 46, 48 expand between the first collapsed configuration and a second, expanded configuration (FIG. 6). This configuration facilitates expansion of intervertebral implant 40 such that anterior end 42 has a greater rate and amount of expansion relative to posterior end 44. It is contemplated that a steeper and/or taller anterior wedge portion facilitates lordosis as intervertebral implant 40 is expanded.

In one embodiment, intervertebral implant 40 can be collapsed from the expanded configuration to an alternate configuration between the expanded and collapsed configurations, via manipulation of wedge 58 in a second axial direction, as shown by arrow B in FIG. 6, opposite to the first axial direction. It is envisioned that reciprocal axial movement of wedge 58 to collapse intervertebral implant 40 may be desired to reposition or remove intervertebral implant 40 from a body cavity. Upon disposal of intervertebral implant 40 in the expanded configuration, to dispose intervertebral implant 40 in an alternate configuration, screw 92 is rotated in a counterclockwise direction such that flange 96 engages wall 98 to draw and axially translate wedge 58, in the second opposing direction shown by arrow B.

As wedge 58 is translated axially in the second axial direction, component 46 pivots about hinge 50 to rotate toward the collapsed configuration such that wedge portions 114, 120 move toward engagement with the respective inclined portions 70, wedge portions 116, 122 move toward engagement with the respective inclined portions 76 and protrusions 118, 124 move toward disposal within the respective recess portions 72. Depending on the application, components 46, 48 may be returned to the fully collapsed configuration, as shown in FIG. 5.

Figure 11:
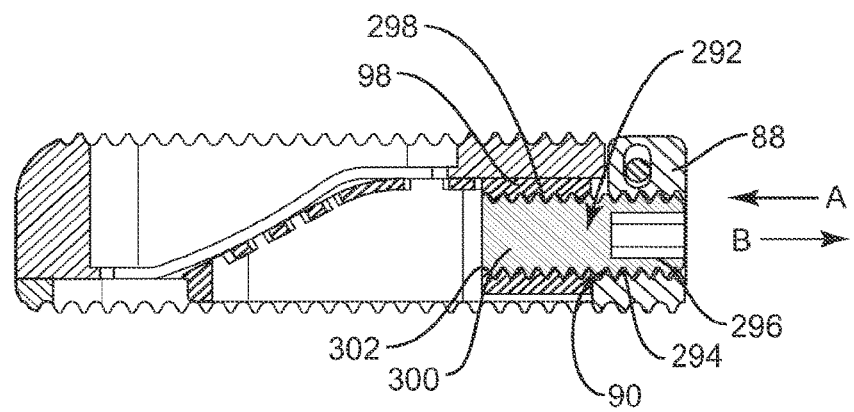
FIG. 11 is a perspective cutaway view of one embodiment of the implant shown in FIG. 1.

In one embodiment, as shown in FIG. 11, an actuator, such as, for example, a turnbuckle 292 including clockwise threads 294 disposed at a proximal end 296 and being configured for disposal within threaded opening 90. Turnbuckle 292 includes counterclockwise threads 298 disposed at a distal end 300 and being configured for threaded engagement with wedge 58. Wall 98 defines a threaded opening 302 configured for disposal of threads 298. From a first collapsed configuration of intervertebral implant 40 described above, turnbuckle 292 is manipulated to move wedge 58 axially. The instrument engages turnbuckle 292 for rotation of threads 294 within threaded opening 90 and rotation of threads 298 within opening 302 to drive expansion of intervertebral implant 40. As turnbuckle 292 rotates, the counter rotation of threads 294, 298 causes turnbuckle 292 to drive apart wedge 58 and base component 48 such that wedge 58 translates axially, as described herein. The surfaces of wedge 58 and components 46, 48 slidably engage as described above such that components 46, 48 expand between the first collapsed configuration and a second, expanded configuration.

Figure 12:
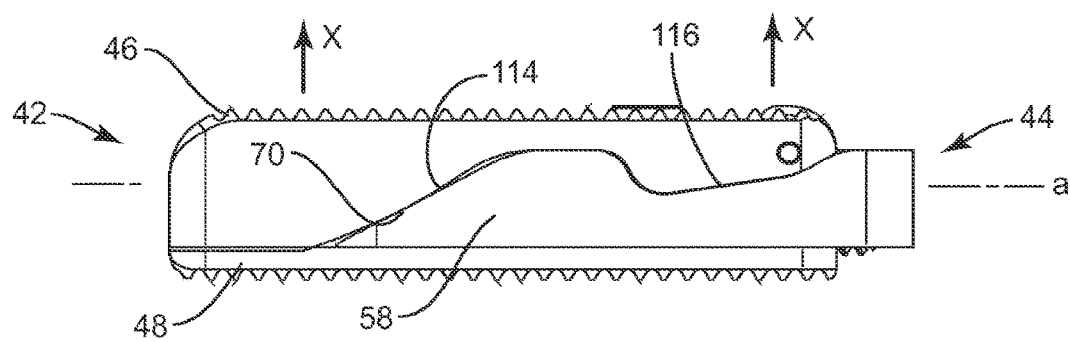
FIG. 12 is a side view of one embodiment of the implant shown in FIG. 1.
Figure 13:
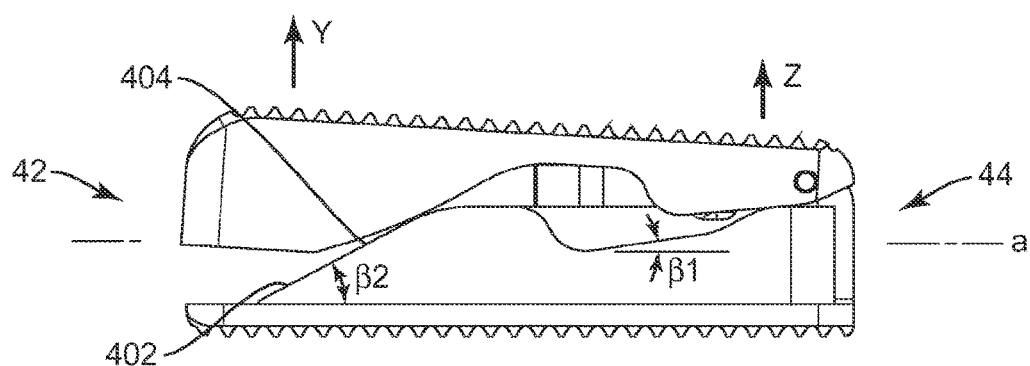
FIG. 13 is a side view of the implant shown in FIG. 12.

In one embodiment, as shown in FIGS. 12 and 13, intervertebral implant 40 is configured for selective and/or variable expansion between the first, collapsed configuration and the second, expanded configuration. It is envisioned that the shape and size of rail portions 110, 112 of wedge 58 can selectively regulate expansion of intervertebral implant 40. Wedge portions 114, 120 each include a first surface 402 having an angle of inclination β1 and a second surface 404 having an angle of inclination β2. Wedge portions 116, 122 have an angle of inclination β1. Angle β2 is greater than angle β1.

Expansion of intervertebral implant 40 between the first and second configurations includes an initial expansion and a secondary expansion. Wedge portions 116, 122 and surfaces 402 of wedge portions 114, 120 have an angle of inclination β1 such that, during the initial expansion, expansion of intervertebral implant 40 adjacent anterior end 42 and posterior end 44 is substantially equivalent, as shown by arrows X. It is contemplated that initial expansion provides decompression of an intervertebral disc space. After a selected amount of expansion, according to the length of surface 402, inclined portion 70 of component 46 engages surfaces 404 of wedge portions 114, 120 to override the expansion due to wedge portions 116, 120. Angle β2 is greater than angle β1 such that anterior end 42, as shown by arrow Y, expands a greater amount relative to posterior end 44, as shown by arrow Z. It is contemplated that the secondary expansion expands an anterior side of an intervertebral disc space a greater amount relative to a posterior side to provide lordosis. It is envisioned that other ramp configurations can be used to expand intervertebral implant 40 in a vertical orientation only, and/or to drive kyphosis in applications such as the thoracic spine.

In assembly and use, the interbody implant system is employed with a surgical procedure, such as, a fusion treatment of a spine of a patient including vertebrae V, intervertebral disc space I and body areas adjacent thereto, as discussed herein. The interbody implant system may also be employed with other surgical procedures, such as, for example, discectomy, laminotomy, laminectomy, nerve root retraction, foramenotomy, facetectomy, decompression, and spinal, nucleus or disc replacement.

Figure 14:
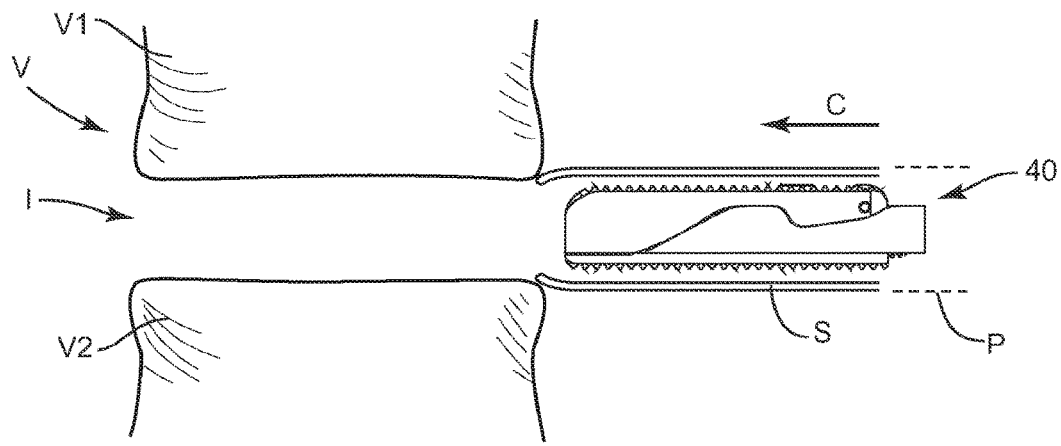
FIG. 14 is a side view of components of a system in accordance with the principles of the present disclosure disposed with vertebrae.
Figure 15:
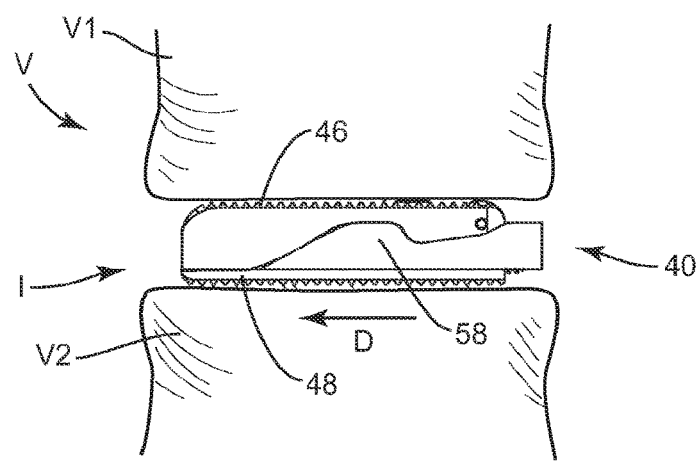
FIG. 15 is a side view of components of the system and vertebrae shown in FIG. 14.
Figure 16:
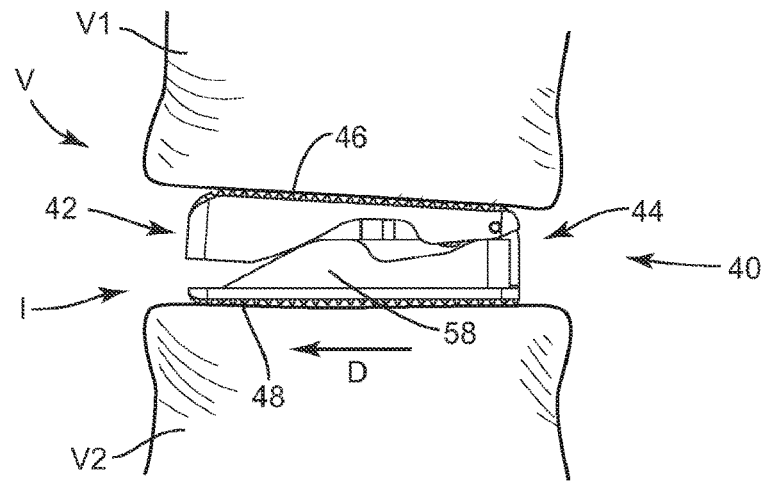
FIG. 16 is a side view of components of the system and vertebrae shown in FIG. 14.
Figure 17:
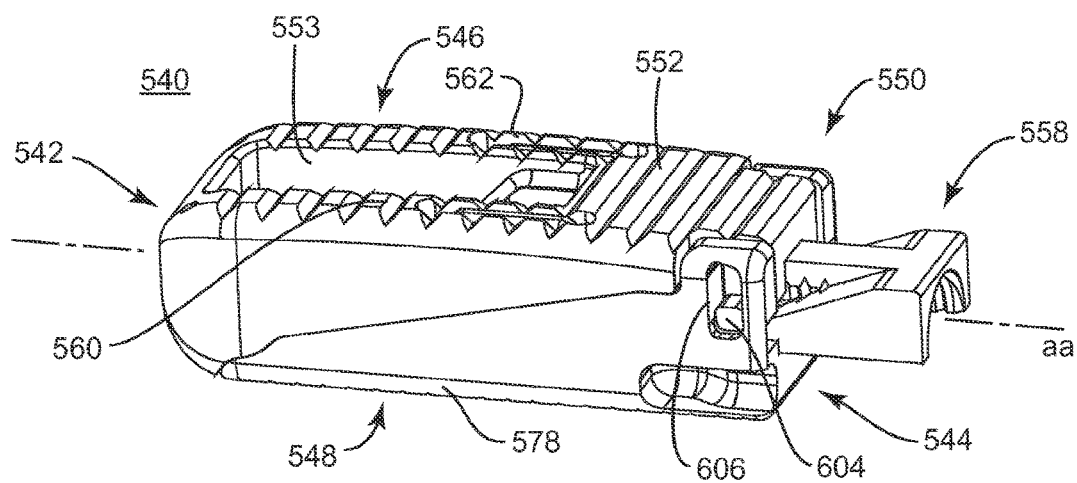
FIG. 17 is a perspective view of one embodiment of the implant shown in FIG. 1.
Figure 18:
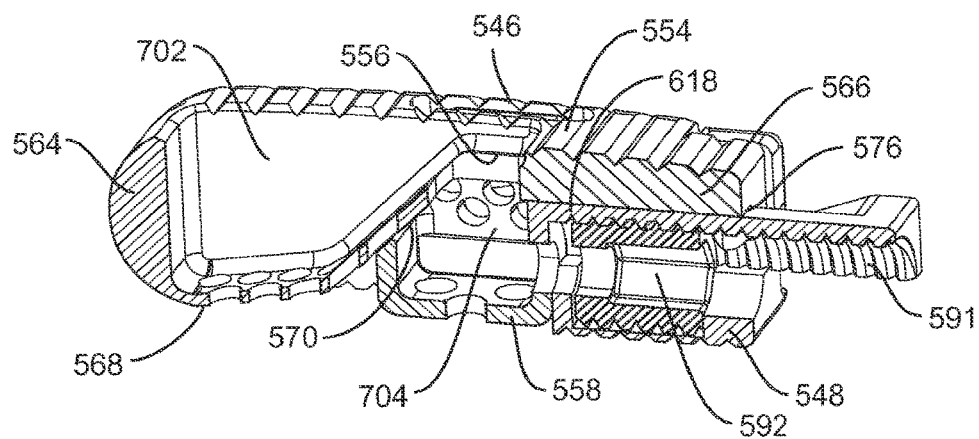
FIG. 18 is a perspective cutaway view of the implant shown in FIG. 17.
Figure 19:
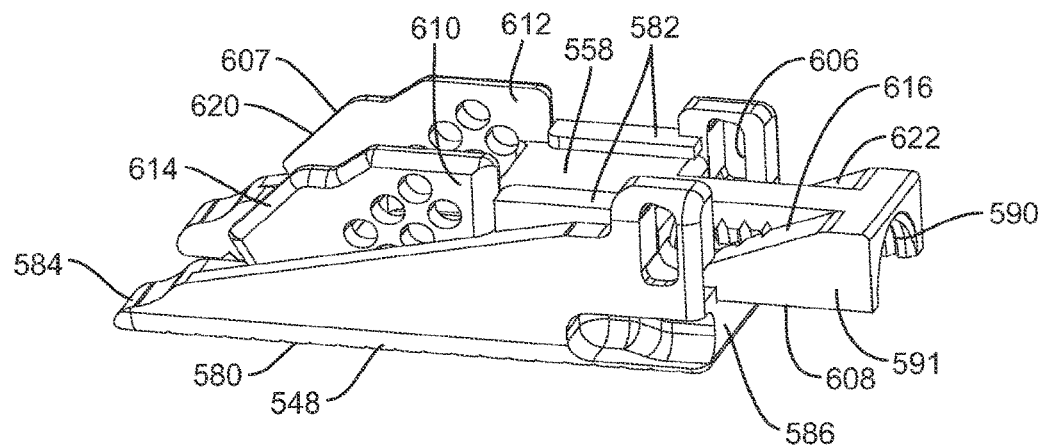
FIG. 19 is a perspective view of components of the implant shown in FIG. 17.

For example, as shown in FIGS. 14-16, the interbody implant system can be employed with a surgical arthrodesis procedure, such as, for example, an interbody fusion for treatment of an applicable condition or injury of an affected section of a spinal column and adjacent areas within a body, such as, for example, intervertebral disc space I between first vertebrae V1 and second vertebrae V2 of vertebrae V. It is contemplated that intervertebral implant 40 of the interbody implant system, described above, can be inserted with intervertebral disc space I to space apart articular joint surfaces, provide support and maximize stabilization of vertebrae V. It is further contemplated that intervertebral implant 40 provides height restoration between vertebral bodies, decompression, restoration of sagittal balance and/or resistance of subsidence into vertebral endplates.

In use, to treat the affected section of vertebrae V, a medical practitioner obtains access to a surgical site including vertebrae V in any appropriate manner, such as through incision and retraction of tissues. It is envisioned that the interbody implant system can be used in any existing surgical method or technique including open surgery, mini-open surgery, minimally invasive surgery and percutaneous surgical implantation, whereby vertebrae V is accessed through a mini-incision, or sleeve that provides a protected passageway to the area. Once access to the surgical site is obtained, the particular surgical procedure is performed for treating the spine disorder. Intervertebral implant 40, described above with regard to FIGS. 1-13, is then employed to augment the surgical treatment. Intervertebral implant 40 can be delivered or implanted as a pre-assembled device or can be assembled in situ. Intervertebral implant 40 can be completely or partially revised, removed or replaced in situ. It is contemplated that one or all of the components of the interbody implant system can be delivered to the surgical site via manual manipulation and/or a free hand technique. It is further contemplated that intervertebral implant 40 may be inserted posteriorly, and then manipulated anteriorly and/or lateral and/or medial.

An incision is made in the body of a patient and a cutting instrument (not shown) creates a surgical pathway P for implantation of intervertebral implant 40 within the patient body. A guide instrument (not shown) is employed to initially distract vertebrae V1 from vertebrae V2, as shown in FIG. 14. A sleeve or cannula S is used to access intervertebral disc space I and facilitate delivery and access for components of the interbody implant system. A preparation instrument (not shown) can be inserted within the sleeve or cannula and disposed within intervertebral disc space I. The preparation instrument(s) can be employed to remove some or all of the disc tissue including the disc nucleus and fluids, adjacent tissues and/or bone, corticate, scrape and/or remove tissue from the surfaces of endplates of opposing vertebrae V1, V2, as well as for aspiration and irrigation of the region according to the requirements of a particular surgical application.

As shown in FIG. 15, intervertebral implant 40 is disposed in the first, collapsed configuration, described above and delivered through surgical pathway P along a substantially posterior approach, as shown by arrow C, into intervertebral disc space I with a delivery instrument (not shown) including a driver. The driver delivers intervertebral implant 40 into the prepared intervertebral disc space I, between vertebrae V1 and vertebrae V2, according to the requirements of a particular surgical application.

Upon desired positioning of intervertebral implant 40, the driver or other instrument engages intervertebral implant 40 to facilitate actuation of the component parts of intervertebral implant 40. The driver engages screw 92 for rotation in a clockwise direction such that screw 92 translates axially to drive wedge 58 axially in the direction shown by arrow D in FIGS. 15 and 16. Wedge portions 114, 120 slidably engage the respective inclined portions 70 of extensions 60, 62 and wedge portions 116, 122 slidably engage the respective inclined portions 76 of extensions 60, 62, as shown and described with regard to FIGS. 5 and 6. Such slidable engagement of the surfaces of wedge 58 and components 46, 48, due to the axial translation of wedge 58, pivots component 46 relative to component 48 in rotation about hinge 50 such that components 46, 48 expand between the first collapsed configuration and a second, expanded configuration, as shown in FIG. 16. This configuration facilitates expansion of intervertebral implant 40 such that anterior end 42 has a greater rate and amount of expansion relative to posterior end 44. It is contemplated that in the expanded configuration, intervertebral implant 40 provides height restoration between vertebrae V1 and vertebrae V2, decompression, restoration of sagittal balance and resistance of subsidence into the endplates of vertebrae V and vertebrae V2.

It is envisioned that the components of the interbody implant system, which may include one or a plurality of intervertebral implants 40, can be delivered to the surgical site via alternate approaches. In one embodiment, intervertebral implant 40 is delivered through the surgical pathway along a transforaminal lumbar interbody fusion approach into intervertebral disc space I and disposed in the expanded configuration. In one embodiment, a plurality of intervertebral implants 40 are delivered through the surgical pathway along a posterior lumbar interbody fusion approach into intervertebral disc space I and disposed in the expanded configuration in a side by side orientation.

In one embodiment, intervertebral implant 40 can be collapsed from the expanded configuration to an alternate configurations between the expanded and collapsed configurations, as described above, to collapse intervertebral implant 40 as may be desired to reposition with or remove intervertebral implant 40 from intervertebral disc space I. In one embodiment, the interbody implant system includes a plurality of intervertebral implants 40, which can be variously sized and configured, and/or oriented in a side by side engagement, spaced apart and/or staggered.

In one embodiment, the interbody implant system includes an agent, which can include a bone growth promoting material, which may be disposed, packed or layered within, on or about the components and/or surfaces of the interbody implant system. The bone growth promoting material, such as, for example, bone graft can be a particulate material, which may include an osteoconductive material such as HA and/or an osteoinductive agent such as a bone morphogenic protein (BMP) to enhance bony fixation of intervertebral implant 40 with the adjacent vertebrae V.

It is contemplated that the agent and/or bone graft may include therapeutic polynucleotides or polypeptides. It is further contemplated that the agent and/or bone graft may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. Intervertebral implant 40 can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

In one embodiment, as shown in FIGS. 17-21, the interbody implant system includes an intervertebral implant 540, similar to intervertebral implant 40 and its components described above with regard to FIGS. 1-16. Intervertebral implant 540 defines a longitudinal axis aa and extends between an anterior end 542 and a posterior end 544. Intervertebral implant 540 includes a piston component 546 and a base component 548 connected to piston component 546. Base component 548 is movably mounted to piston component 546 with a hinge 550 to facilitate a pivoting connection between components 546, 548. Components 546, 548 are relatively movable to expand and collapse with intervertebral implant 540 between a first configuration and a second configuration, as will be described.

Piston component 546 includes an endplate surface 552. Endplate surface 552 defines a substantially rectangular opening 553. Endplate surface 552 is configured to engage an endplate of a vertebra and includes a plurality of raised elements 554 configured to enhance fixation and/or gripping with vertebral tissue. Elements 554 are disposed transverse to longitudinal axis aa.

Piston component 546 includes an inner surface 556 disposed to face an opposing orientation and/or direction relative to the facing orientation and/or direction of endplate surface 552. Endplate surface 552 is oriented in a direction to face tissue of a vertebral endplate and inner surface 556 is oriented to face an opposite direction. Inner surface 556 is substantially smooth or even and configured to engage a surface of a wedge 558 such that wedge 558 is movable relative to components 546, 548.

Piston component 546 includes a first extension 560 and a second extension 562 extending in a substantially linear configuration along longitudinal axis aa between an anterior end 564 and a posterior end 566. Extensions 560, 562 are monolithically formed with ends 564, 566. Extensions 560, 562 are disposed in a substantially parallel orientation relative to longitudinal axis aa.

Each of extensions 560, 562 include at least a portion of inner surface 556 that engages at least a portion of the surface of wedge 558 to expand and collapse intervertebral implant 540 between a first configuration and a second configuration. Each of extensions 560, 562 include a portion 568 that engages base component 548, an inclined portion 570 and a linear portion 576. Portions 568, 570, 576 are disposed in series along each of extensions 560, 562. Inclined portion 570 is disposed at an angle from axis aa.

Base component 548 includes an endplate surface 578. Endplate surface 578 is configured to engage an endplate of a vertebra and includes a plurality of raised elements 580 configured to enhance fixation and/or gripping with vertebral tissue. Elements 580 are disposed transverse to longitudinal axis aa. Base component 548 includes a wall 582 defining an inner surface configured to support slidable movement of wedge 558. Wall 582 is disposed on opposing lateral sides of intervertebral implant 540 such that wedge 558 is movable within an inner surface boundary of base component 548. Endplate surface 578 is oriented in a direction to face tissue of a vertebral endplate and wall 582 is oriented to face wedge 558. Wedge 558 is movable relative to components 546, 548 within the inner surface boundary of base 548.

Base component 548 extends in a substantially linear configuration along longitudinal axis as between an anterior end 584 and a posterior end 586. Posterior end 586 includes wall portions 588 that supports an actuator, such as, for example, a threaded screw 592. Wall portions 588 fix the position of screw 592 with base component 548 and facilitate free rotation of screw 592 between wall portions 588. Screw 592 is configured for disposal between wall portions 588 and a threaded cavity, such as, for example, threaded slot 590 defined by a wall 591 of wedge 558.

Screw 592 is rotatable relative to wall portions 588 and wall 591 in a first direction, such as clockwise, and a second opposing direction, such as counter clockwise. Screw 592 is configured to mate with threaded slot 590 in a threaded engagement and freely rotatable therein. Screw 592 is rotated in a clockwise direction such that engagement with slot 590 axially translates wedge 558, in a first direction shown by arrow AA in FIGS. 20 and 21. Screw 592 is rotated in a counter clockwise direction such that engagement with slot 590 axially translates wedge 558, in a second opposing direction shown by arrow BB.

Screw 592 is fixed with component 548 to effect axial translation of wedge 558 such that wedge 558 is movable relative to components 546, 548 to expand and collapse intervertebral implant 540 between a first configuration and a second configuration. Screw 592 is engaged with an instrument or tool (not shown), to facilitate actuation of the component parts of intervertebral implant 540 and disposal thereof in various configurations according to the requirements of a particular application.

Base component 548 is pivotably connected to piston component 546 adjacent posterior ends 566, 586 with hinge 550 to facilitate a pivoting connection between components 546, 548. Posterior end 566 includes a pin 604 configured for disposal within an elongated slot 606 of posterior end 586. Pin 604 is movable along an axis transverse to longitudinal axis aa along slot 606 to facilitate expansion and collapse of intervertebral implant 540 between a first configuration and a second configuration.

Wedge 558 is disposed in an intermediate orientation with components 546, 548. Wedge 558 includes a first surface 607 that engages component 546 and a second surface 608 that engages component 548 such that wedge 558 is movable for axial translation relative to components 546, 548. Wedge 558 includes a first rail portion 610 and a second rail portion 612, disposed along longitudinal axis aa, which movably engage components 546, 548 to expand and collapse intervertebral implant 540 between a first configuration and a second configuration.

Rail portion 610 includes a first ramp, such as, for example, an anterior wedge portion 614 and a second ramp, such as, for example, a posterior wedge portion 616. Anterior wedge portion 614 is axially spaced apart from posterior wedge portion 616 along rail portion 610. Anterior wedge portion 614 has a height and an angle of inclination relative to longitudinal axis aa, similar to that described above. Posterior wedge portion 616 has a height and an angle of inclination relative to axis aa, similar to that described above.

Rail portion 610 includes a member 618 disposed between wedge portions 614, 616 such that wedge portions 614, 616 are axially spaced apart. Member 618 connects wedge portion 614 with wedge portion 616. Wedge portions 614, 616 and member 618 are disposed in series along rail portion 610. It is contemplated that wedge portions 614, 616 drive apart components 546, 548 at anterior end 542 and posterior end 544 to facilitate expansion and collapse of intervertebral implant 540 between a first configuration and a second configuration. It is further contemplated that the height and/or angle of wedge portions 614, 616 regulates the amount and rate of expansion of intervertebral implant 540 at least adjacent rail portion 610. It is envisioned that wedge portions 614, 616 are monolithically formed, connected by fastening elements or separate and distinct structure.

Rail portion 612 includes a third ramp, such as, for example, an anterior wedge portion 620 and a fourth ramp, such as, for example, a posterior wedge portion 622. Anterior wedge portion 620 is axially spaced apart from posterior wedge portion 622 along rail portion 612. Wedge portions 620, 622 each have a height and angle of inclination, similar to that described above.

Member 618 is disposed between wedge portions 620, 622 such that wedge portions 620, 622 are axially spaced apart. Member 618 connects wedge portion 620 with wedge portion 622. Wedge portions 620, 622 and member 618 are disposed in series along rail portion 612. It is contemplated that wedge portions 620, 622 drive apart components 546, 548 at anterior end 542 and posterior end 544 to facilitate expansion and collapse of intervertebral implant 540 between a first configuration and a second configuration. It is further contemplated that the height and/or angle of wedge portions 620, 622 regulates the amount and rate of expansion of intervertebral implant 540 at least adjacent rail portion 612. It is envisioned that wedge portions 620, 622 are monolithically formed, connected by fastening elements or separate and distinct structure.

Each of rail portions 610, 612 include at least a portion of first surface 607 that engages at least a portion of inner surface 556 of component 546 to expand and collapse intervertebral implant 540 between a first configuration and a second configuration. The portions of surface 607 including wedge portions 614, 616 disposed along rail portion 610 slideably engage portions 570, 576 disposed along extension 560. The portions of surface 607 including wedge portions 620, 622 disposed along rail portion 612 slideably engage portions 570, 576 disposed along extension 562.

Rail portions 610, 612 extend in a proximal and/or posterior direction for disposal within wall portions 582 adjacent posterior end 544. Rail portions 610, 612 move within wall portions 582 during axial translation of the component parts of intervertebral implant 40.

Piston component 548 includes a receptacle, such as, for example, a basket 702 configured for disposal of at least one agent, for example, bone graft. Wedge 558 includes a receptacle, such as, for example, a basket 704 configured for disposal of at least one agent, for example, bone graft. In the first, collapsed configuration, baskets 702, 704 are disposed in series in a side by side configuration. As intervertebral implant 540 is expanded to the second, expanded configuration, baskets 702, 704 translate to a vertical stacked configuration such that bone graft can grow through the connected baskets 702, 704. Each of baskets 702, 704 include a plurality of openings that allow bone to grow between baskets 702, 704.

Figure 20:
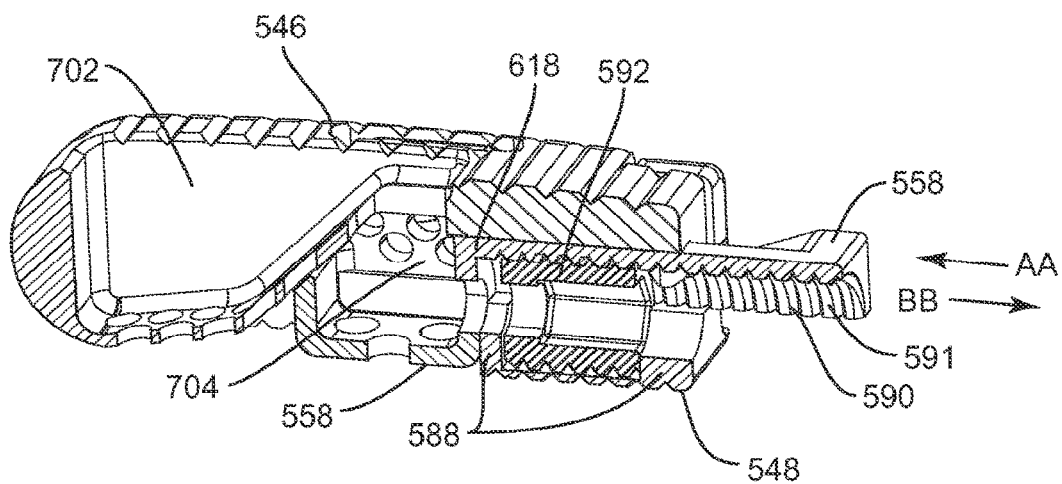
FIG. 20 is a perspective cutaway view of the implant shown in FIG. 17.
Figure 21:
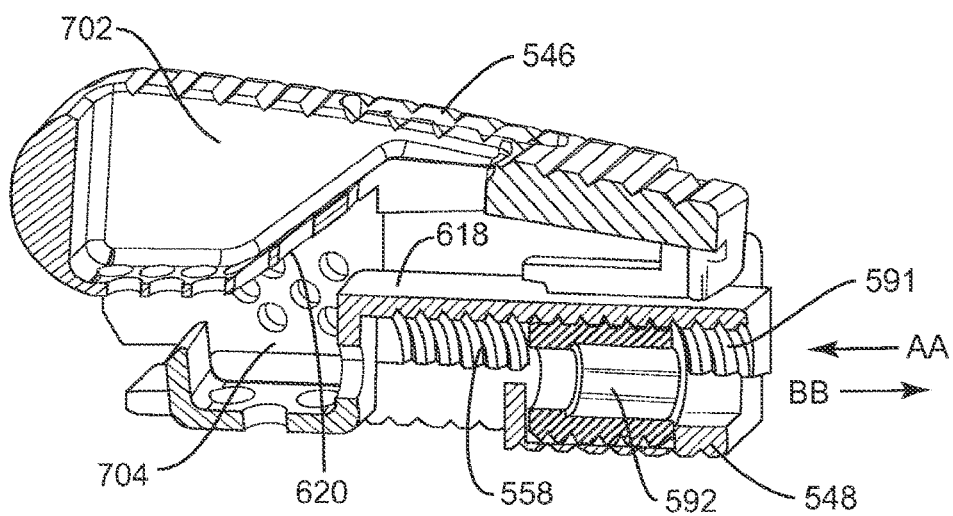
FIG. 21 is a perspective cutaway view of the implant shown in FIG. 17.
Figure 22:
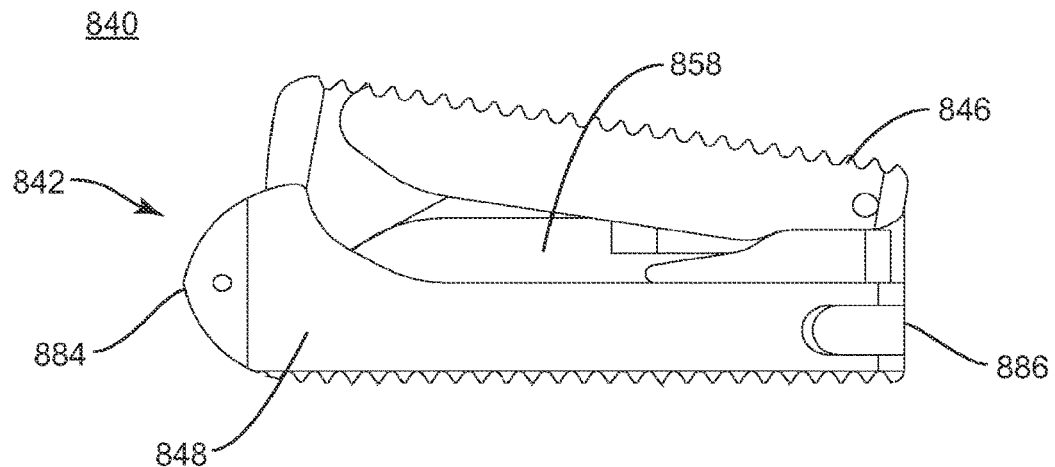
FIG. 22 is a perspective view of one embodiment of the implant shown in FIG. 1.
Figure 23:
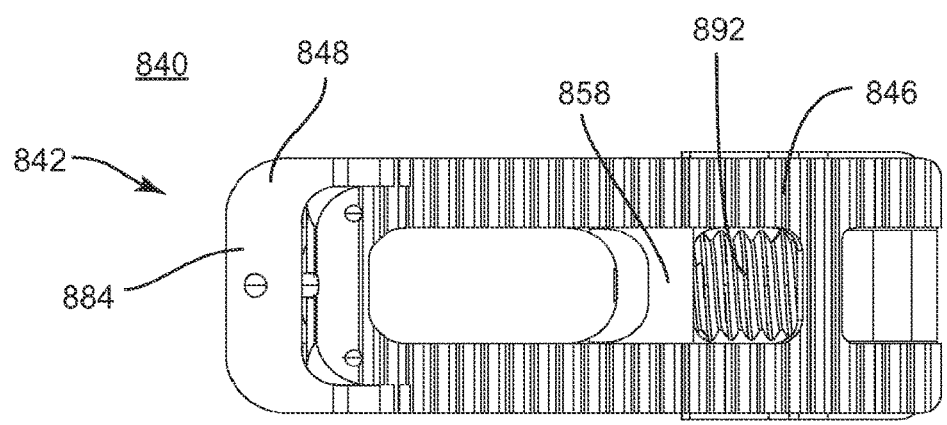
FIG. 23 is a plan view of the implant shown in FIG. 22.
Figure 24:
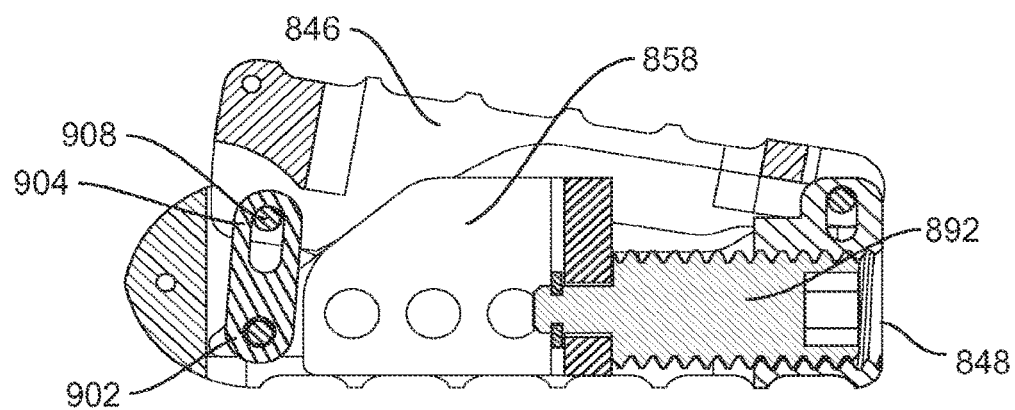
FIG. 24 is a side cross section view of the implant shown in FIG. 22.
Figure 25:
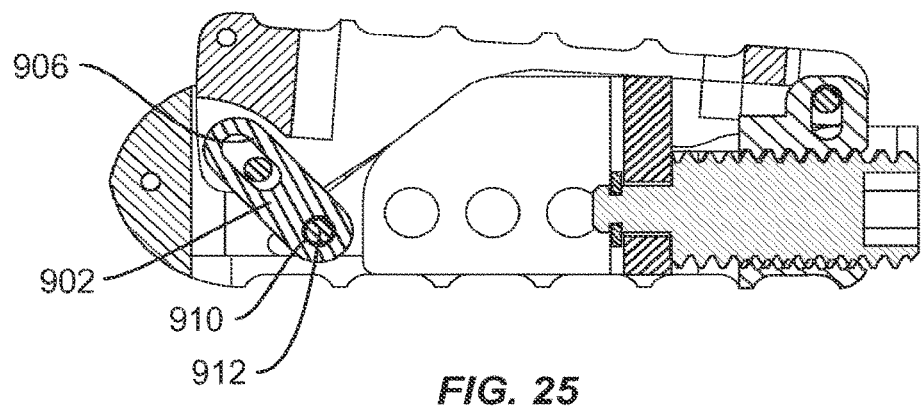
FIG. 25 is a side cross section view of the implant shown in FIG. 22.

In operation, as shown in FIGS. 20 and 21, intervertebral implant 540 is engaged for disposal between a first configuration and a second configuration such that intervertebral implant 540 expands in an intervertebral disc space. Intervertebral implant 540 is engaged with an instrument (not shown) to facilitate actuation of the component parts of intervertebral implant 540 according to the requirements of a particular surgical application.

In a first configuration, such as, for example, a collapsed configuration (FIG. 20), components 546, 548 are disposed in a low profile orientation with wedge 558. Upon desired positioning of intervertebral implant 540 according to the requirements of a particular surgical application, screw 592 is manipulated to move wedge 558 axially, as described above. As wedge 558 axially translates in the direction shown by arrow AA, wedge portions 614, 620, 616, 622 slidably engage extensions 560, 562. Such slidable engagement of the surfaces of wedge 558 and components 546, 548, due to the axial translation of wedge 558, pivots component 546 relative to component 548 in rotation about hinge 550 such that components 546, 548 expand between the first collapsed configuration and a second, expanded configuration (FIG. 21). This configuration facilitates expansion of intervertebral implant 540 such that anterior end 542 has a greater rate and amount of expansion relative to posterior end 544.

In one embodiment, intervertebral implant 540 can be collapsed from the expanded configuration to an alternate configuration between the expanded and collapsed configurations, via manipulation of wedge 558 in a second axial direction, as shown by arrow BB in FIGS. 20 and 21, opposite to the first axial direction. It is envisioned that reciprocal axial movement of wedge 558 to collapse intervertebral implant 540 may be desired to reposition or remove intervertebral implant 540 from a body cavity. Upon disposal of intervertebral implant 540 in the expanded configuration, to dispose intervertebral implant 540 in an alternate configuration, screw 592 is rotated in a counter-clockwise direction such that wedge 558 axially translates, in the second opposing direction shown by arrow B. As wedge 558 is translated axially in the second axial direction, component 546 pivots about hinge 550 to rotate toward the collapsed configuration.

In one embodiment, as shown in FIGS. 22-26, the interbody implant system includes an intervertebral implant 840, similar to intervertebral implant 40 and intervertebral implant 540 and their components described above. Intervertebral implant 840 includes a base component 848 having a posterior end 886 configured to attach to an inserter or tool (not shown) that engages a screw 892 for axially translating a wedge 858. Base component 848 includes a wedge shaped anterior end 884. Base component 848 protects wedge 858 and screw 892 as intervertebral implant 840 is inserted into an intervertebral disc space. It is contemplated that forces employed to introduce or deliver intervertebral implant 840 to the intervertebral disc space are transmitted through the inserter to an anterior end 842 of intervertebral implant 840. A piston component 846 includes an opening 847 and base component 848 includes an opening 849. Openings 847, 849 are configured to receive radio-opaque markers.

Intervertebral implant 840 includes a linkage component 902 that connects piston component 846 to wedge 858. Linkage component 902 has a first end 904 including a slot 906 that supports a pin 908 of piston component 846. Pin 908 is slidably supported with slot 906 for movement therein. Linkage component 902 has a second end 910 connected by a pin 912 with wedge 858.

Figure 26:
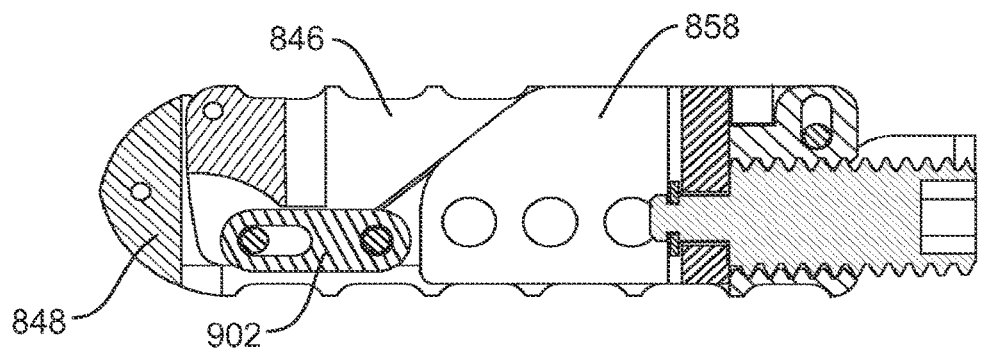
FIG. 26 is a side cross section view of the implant shown in FIG. 22.

Linkage component 902 has a passive configuration as intervertebral implant 840 is expanded to the second, expanded configuration (FIG. 24), as described above with regard to intervertebral implants 40, 540. In applications that require intervertebral implant 840 to be collapsed, as described herein, the linkage draws piston component 846 into the collapsed configuration (FIG. 26). Linkage component 902 facilitates disposal of intervertebral implant 840 from the expanded configuration for removal or repositioning of intervertebral implant 840 in the intervertebral disc space. It is envisioned that linkage component 902 prevents bone graft and/or agents from undesirably engaging and/or interfering with wedge 858 during axial translation. Wedge 858 includes openings 859 that reduce material to reduce medical imaging scatter.

Figure 27:
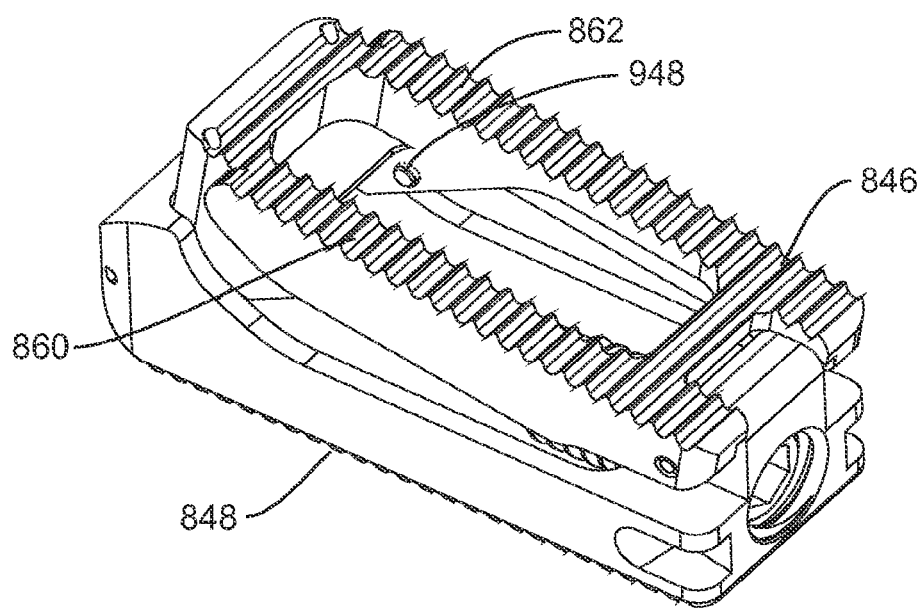
FIG. 27 is a perspective view of one embodiment of the components of the implant shown in FIG. 22.
Figure 28:
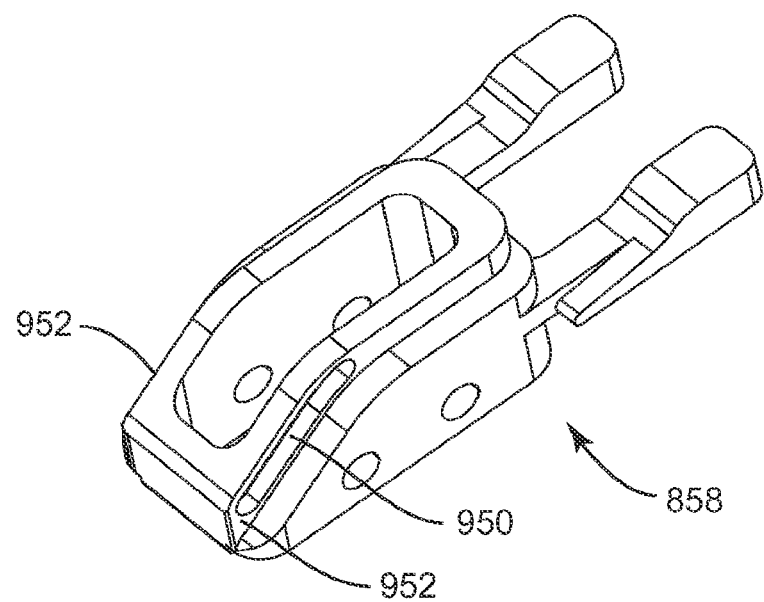
FIG. 28 is a perspective view of a component of the implant shown in FIG. 22.

In one embodiment, as shown in FIGS. 27 and 28, intervertebral implant 840 can be actively collapsed employing a pin and channel configuration. Piston component 846 includes pins 948 extending inwardly from extensions 860, 862. Pins 948 are disposed within channels 950 formed in opposing side walls 952 of wedge 858. Pins 948 are disposed for slidable movement within the configuration of channels 950. As intervertebral implant 840 is collapsed, as described herein, wedge 858 is retracted via axial translation. Channels 950 selectively guide pins along wedge 858 to draw piston component 846 into the collapsed configuration. It is envisioned that wedge 858 may include pins and piston component 846 includes channels for drawing piston component 846 into the collapsed configuration. It is further envisioned that wedge 858 may include a dovetail member for slidable movement within channels 950.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An intervertebral implant comprising:
   a first component extending along a longitudinal axis and comprising an outer tissue engaging surface and an inner surface;
   a second component connected to the first component such that the first component is pivotable relative to the second component about a pin extending transverse to the longitudinal axis through openings in the first and second components, the second component comprising an outer tissue engaging surface and an inner surface, the second component including an actuator; and
   a third component disposed for engagement and being movable relative to the first and second components, the third component comprising at least a first ramp and a second ramp axially spaced apart from the first ramp,
   wherein the actuator is engageable with the third component to effect axial translation of the third component such that the ramps engage the inner surface of one of the first component and the second component to move the first component between a first, collapsed configuration and a second, expanded configuration,
   wherein the third component comprises a first surface that includes the ramps and an opposite planar second surface,
   wherein the inner surface of the second component is planar and engages the second surface as the first component moves between the first, collapsed configuration and the second, expanded configuration,
   wherein the first component extends along the longitudinal axis between opposite first and second ends of the first component, the second component comprising a first end that is connected to the first end of the first component, the intervertebral implant further comprising a linkage component connected to the second end of the first component and a second end of the second component,
   wherein the linkage component has a first end including a slot that supports a pin of the first component, the pin being slidably supported with the slot for movement therein and
   wherein the linkage component has a second end that is connected by a pin with the third component.

2. An intervertebral implant as recited in claim 1, wherein the inner surface of the first component comprises first and second inclined portions that slide along the first and second ramps as the first component moves between the first, collapsed configuration and the second, expanded configuration.

3. An intervertebral implant as recited in claim 2, wherein the inclined portions extend at an acute angle relative to the longitudinal axis.

4. An intervertebral implant as recited in claim 2, wherein the first inclined portion extends at a first angle relative to the longitudinal axis and the second inclined portion extends at a second angle relative to the longitudinal axis, the first angle being greater than the second angle.

5. An intervertebral implant as recited in claim 4, wherein the first angle is 30 to 60 degrees and the second angle is 4 to 30 degrees.

6. An intervertebral implant as recited in claim 1, wherein the actuator comprises a distal end and an opposite proximal end that includes a tool socket.

7. An intervertebral implant as recited in claim 6, wherein the pin extending transverse to the longitudinal axis through the openings in the first and second components is spaced apart from the third component and the distal end of the actuator comprises a flange that engages a wall of the third component to retain the actuator with the third component and effect translation of the third component in opposite directions along the longitudinal axis.

8. An intervertebral implant as recited in claim 1, wherein the first component comprises a first rail, a second rail and spaced apart first and second transverse walls that connect the first rail with the second rail, a wall of the second component being positioned between the rails, the pin extending transverse to the longitudinal axis through the openings in the first and second components extending through the wall and the rails to connect the first component with the second component.

9. An intervertebral implant as recited in claim 1, wherein the actuator is a threaded screw that is positioned within a threaded opening in the second component.

10. An intervertebral implant as recited in claim 1, wherein the pin extending transverse to the longitudinal axis through the openings in the first and second components is disposed within an elongated slot of the second component such that the pin extending transverse to the longitudinal axis through the openings in the first and second components translates within the elongated slot as the first component moves between the first, collapsed configuration and the second, expanded configuration.

11. An intervertebral implant as recited in claim 10, wherein the pin extending transverse to the longitudinal axis through the openings in the first and second components moves from a first end of the elongated slot to an opposite second end of the elongated slot as the first component moves between the first, collapsed configuration and the second, expanded configuration.

12. An intervertebral implant as recited in claim 1, wherein the actuator is fixed with the third component.

13. An intervertebral implant as recited in claim 1, wherein the second and third components each comprise a basket configured for disposal of bone graft, the basket being disposed in series in a side by side configuration when the components are in the first, collapsed configuration and in a vertical stacked configuration when the first component is in the second, expanded configuration.

14. An intervertebral implant as recited in claim 1, wherein the implant comprises a cavity that extends through the first, second and third components, the cavity having a constant volume as the first component moves between the first, collapsed configuration and the second, expanded configuration.

15. An intervertebral implant as recited in claim 1, wherein the inner surface of the first component engages the inner surface of the second component when the first component is in the first, collapsed configuration and the inner surface of the first component is spaced apart from the inner surface of the second component when the first component is in the second, expanded configuration.

16. An intervertebral implant as recited in claim 1, wherein the linkage component extends parallel to the longitudinal axis when the first component is in the first, collapsed configuration, the linkage component extending transverse to the longitudinal axis when the first component is in the second, expanded configuration.

17. An intervertebral implant comprising:
a first component extending along a longitudinal axis between opposite first and second ends and comprising an inner surface having spaced apart first and second inclined portions;
a second component pivotably connected with the first component and comprising opposite first and second ends, the first end of the second component being connected to the first end of the first component about a pin extending through openings in the first and second components;
a linkage component connected to the second end of the first component and the second end of the second component;
a third component positioned between the first and second components, the third component comprising at least a first ramp and a second ramp axially spaced apart from the first ramp; and
an actuator that extends through the second component and into the third component to fix the actuator with the third component, the actuator being rotatable relative to the second component and comprising a threaded outer surface that engages a threaded inner surface of the second component,
wherein rotation of the actuator relative to the second member causes the third member to translate axially relative to the first and second members such that the ramps slide along the inclined portions to move the first component from a first, collapsed configuration to a second, expanded configuration, the linkage component extending parallel to the longitudinal axis when the first component is in the first, collapsed configuration, the linkage component extending transverse to the longitudinal axis when the first component is in the second, expanded configuration.

18. An intervertebral implant comprising:
a first component extending along a longitudinal axis and comprising an outer tissue engaging surface and an inner surface;
a second component connected to the first component such that the first component is pivotable relative to the second component about a pin extending transverse to the longitudinal axis through openings in the first and second components, the second component comprising an outer tissue engaging surface and an inner surface, the second component including an actuator comprising a distal end and an opposite proximal end that includes a tool socket; and
a third component disposed for engagement and being movable relative to the first and second components, the third component comprising at least a first ramp and a second ramp axially spaced apart from the first ramp,
wherein the pin is spaced apart from the third component and the distal end of the actuator comprises a flange that engages a wall of the third component to retain the actuator with the third component and effect translation of the third component in opposite directions along the longitudinal axis,
wherein the actuator is engageable with the third component to effect axial translation of the third component such that the ramps engage the inner surface of one of the first component and the second component to move the first component between a first, collapsed configuration and a second, expanded configuration,
wherein the third component comprises a first surface that includes the ramps and an opposite planar second surface, and
wherein the inner surface of the second component is planar and engages the second surface as the first component moves between the first, collapsed configuration and the second, expanded configuration.

19. An intervertebral implant as recited in claim 18, wherein the inner surface of the first component comprises first and second inclined portions that slide along the first and second ramps as the first component moves between the first, collapsed configuration and the second, expanded configuration.

20. An intervertebral implant as recited in claim 19, wherein the inclined portions extend at an acute angle relative to the longitudinal axis.

* * * * *

UNITED STATES PATENT AND TRADEMARK OFFICE
CERTIFICATE OF CORRECTION

| | | |
|---|---|---|
| PATENT NO. | : 10,195,050 B2 | Page 1 of 1 |
| APPLICATION NO. | : 15/263604 | |
| DATED | : February 5, 2019 | |
| INVENTOR(S) | : Palmatier et al. | |

It is certified that error appears in the above-identified patent and that said Letters Patent is hereby corrected as shown below:

In the Specification

In Column 1, Line 8, delete "2011," and insert -- 2011, now Pat. No. 9,445,919, --, therefor.

In Column 2, Line 27, delete "actuator, and" and insert -- actuator; and --, therefor.

In Column 3, Line 10, delete "FIG. 1:" and insert -- FIG. 1; --, therefor.

In Column 3, Line 20, delete "FIG. 1:" and insert -- FIG. 1; --, therefor.

In Column 6, Line 42, delete "piston component 42" and insert -- piston component 46 --, therefor.

In Column 10, Lines 4-5, delete "piston component 48" and insert -- piston component 46 --, therefor.

In Column 14, Line 24, delete "vertebrae V" and insert -- vertebrae V1 --, therefor.

In Column 16, Line 9, delete "longitudinal axis as" and insert -- longitudinal axis aa --, therefor.

Signed and Sealed this
Sixteenth Day of April, 2019

Andrei Iancu
*Director of the United States Patent and Trademark Office*